US008244476B2

(12) United States Patent
Zhang et al.

(10) Patent No.: US 8,244,476 B2

(45) Date of Patent: Aug. 14, 2012

(54) HEPATIC DISEASE-EVALUATING APPARATUS, HEPATIC DISEASE-EVALUATING METHOD, HEPATIC DISEASE-EVALUATING SYSTEM, HEPATIC DISEASE-EVALUATING PROGRAM AND RECORDING MEDIUM

(75) Inventors: Qingwei Zhang, Kawasaki (JP); Mitsuo Takahashi, Kawasaki (JP); Tetsuya Sugimoto, Kawasaki (JP); Yasushi Noguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 296 days.

(21) Appl. No.: 11/987,415

(22) Filed: Nov. 29, 2007

(65) Prior Publication Data

US 2008/0154515 A1 Jun. 26, 2008
US 2011/0282585 A9 Nov. 17, 2011

Related U.S. Application Data

(63) Continuation of application No. PCT/JP2006/310164, filed on May 22, 2006, and a continuation-in-part of application No. 11/148,352, filed on Jun. 9, 2005, which is a continuation of application No. PCT/JP2003/015713, filed on Dec. 9, 2003.

(30) Foreign Application Priority Data

Dec. 9, 2002 (JP) ................................ 2002-357042
Aug. 1, 2003 (JP) ................................ 2003-205589
May 30, 2005 (JP) ................................ 2005-157802

(51) Int. Cl.
*G06F 19/00* (2011.01)
*A61K 38/00* (2006.01)

(52) U.S. Cl. ........................................ 702/19; 530/300

(58) Field of Classification Search .................... 702/19, 702/22, 23, 30, 32, 179, 181, 183; 424/439; 514/215, 292; 703/11

See application file for complete search history.

(56) References Cited

U.S. PATENT DOCUMENTS

| | | | | |
|---|---|---|---|---|
| 6,631,330 | B1 | 10/2003 | Poynard | |
| 2004/0022827 | A1* | 2/2004 | Satomi et al. | 424/439 |
| 2005/0124865 | A1 | 6/2005 | Kawanishi | |
| 2005/0214885 | A1 | 9/2005 | Yamakoshi et al. | |
| 2005/0283347 | A1* | 12/2005 | Kimura et al. | 703/11 |
| 2007/0218519 | A1 | 9/2007 | Urdea et al. | |
| 2008/0147368 | A1 | 6/2008 | Sugimoto et al. | |
| 2010/0173348 | A1 | 7/2010 | Tanaka et al. | |

FOREIGN PATENT DOCUMENTS

| | | | |
|---|---|---|---|
| EP | 1 570 779 | A1 | 9/2005 |
| EP | 2 172 775 | A1 | 4/2010 |
| JP | 61-126472 | A | 6/1986 |
| JP | 2000-298131 | A | 10/2000 |
| JP | 2001-190299 | A | 7/2001 |
| WO | WO 03/083133 | A1 | 9/2003 |
| WO | WO 2004/052191 | A1 | 6/2004 |
| WO | WO 2006/098192 | A1 | 9/2006 |
| WO | WO 2009/001862 | A1 | 12/2008 |

OTHER PUBLICATIONS

Fischer et al., "The role of plasma amino acids in hepatic encephalopathy," Surgery, Sep. 1975, 78(3):276-290.

Luo et al., "Simple Blood Tests Can Predict Compensated Liver Cirrhosis in Patients with Chronic Hepatitis C," Hepato-Gastroenterology, 2002, 49:478-481.

Pohl et al., "Serum Aminotransferase Levels and Platelet Counts as Predictors of Degree of Fibrosis in Chronic Hepatitis C Virus Infection," American Journal of Gastroenterology, 2001, 96(11):3142-3146.

Wai et al., "A Simple Noninvasive Index Can Predict Both Significant Fibrosis and Cirrhosis in Patients with Chronic Hepatitis C," Hepatology, 2003, 38(2):518-526.

Supplementary Partial European Search Report dated Dec. 29, 2009, in corresponding EP 06746698.7, 6 pages.

Zhang et al., "Plasma amino acid profiles applied for diagnosis of advanced liver fibrosis in patients with chronic hepatitis C infection," Hepatology Research, 2006, 34:170-177.

Morgan et al., "Plasma amino-acid patterns in liver disease," Gut, 1982, 23:362-370.

Albert et al., "The metabolic Syndrome—a new worldwide definition," The Lancet, Sep. 24, 2005, 366:1059-1062.

Amamiya et al., "Negative correlations between free histidine content in plasma and BMI or area of vesceral fat," JPFNI, 2008, 18(2):87-91.

Caballero et al., "Plasma amino acid concentrations in healthy elderly men and women," Am. J. Clin. Nutr., 1991, 53(6):1249-1252.

Evans et al., "Maternal and fetal amino acid concentrations during pre-eclampsia." Reproduction, 2003, 125:785-790.

Fortunato et al., "Multivariate Discriminant Function Based on Six Biochemical Markers in Blood Can Predict the Cirrhotic Evolution of Chronic Hepatitis," Clinical Chemistry, 2001, 47(9):1696-1700.

Horie et al., "New Body Mass Index Criteria of Central Obesity for Male Japanese," Tohoku J. Exp. Med., 2006, 208:83-86.

Isomaa et al., "Cardiovascular Morbidity and Mortality Associated with the Metabolic Syndrome." Diabetes Care, Apr. 2001, 24(4):683-689. Kono et al., "Seikagakuteki kensa [1] D, Teibunshi Chisso Kagobutsu Kankei Amino acid to Sono Bunkaku," Japanese Journal of Clinical Medicine, 2004, 62(11):567-570, with partial English translation as indicated.

Matsuzawa et al. (The Examination Committee of Criteria for 'Obesity disease' in Japan, Japan Society for the Study of Obesity). "New Criteria for 'Obesity disease' in Japan," Circ. J., 2002, 66(11):967-992.

Metabolic Syndrome Diagnostic Criteria Examination Committee, "Metabolic Syndrome Definition and Health Standard," The Journal of Japanese Society of Internal Medicine, Apr. 10, 2005, 94:794-809, with partial English translation as indicated.

(Continued)

*Primary Examiner* — Lori A Clow

(74) *Attorney, Agent, or Firm* — Foley & Lardner LLP

(57) ABSTRACT

In a hepatic disease-evaluating apparatus, an indicator calculating unit calculates an index indicating the degree of hepatic fibrosis from amino acid concentration data to be evaluated including amino acid concentration value, based on one or more indices of fractional expression having amino acid concentration as variable. A disease state evaluating unit evaluates the disease state of the hepatic disease to be evaluated, based on the index value.

42 Claims, 17 Drawing Sheets

OTHER PUBLICATIONS

Minoru et al., "Comparative Studies on Blood Amino Acid Level in Normal, Seemingly Obese, Odcult Obese, and Obese." The Journal of the Japanese Society of Internal Medicine, Feb. 20, 2009, 98(special extra issue):233, with English translation.

Noguchi et al., "Network analysis of plasma and tissue amino acids and the generation of an amino index for potential diagnostic use." Am. J. Clin. Nutr., Feb. 2006, 83(2):513S-519S.

Piji et al., "Insulin-induced Decline of Plasma Amino Acid Concentrations in Obese Subjects With and Without Non-Insulin-Dependent Diabetes." Metabolism, May 1994, 43(5):640-646.

Proenza et al. "Blood amino acid compartmentation in men and women with different degrees of obesity," J. Nutr. Biochem, 1998, 9(12):697-704.

Rocca et al., "Sex Differences in the Effect of Obesity on Human Plasma Tryptophan/Large Neutral Amino Acid Ratio," Ann. Nutr. Metab., 1999, 43:145-151.

Sakurai et al., "Analysis on Blood Amino Acid Level in Obese Person," Japanese Journal of Cardiovascular Disease Prevention, Apr. 30, 2009, 44(2):109, with English translation.

Takahashi et al., "Ningen Dock ni Okeru Kessho Amino acid Sokutei no Yuyosei ni Tsuitel: Metabolic Syndrome Kenshin," Ningen dock, 2006, 21(2):589. 2-6-33, with English translation.

* cited by examiner

| USER ID | USER PASSWORD | NAME | ORGANI-ZATION ID | DEPART-MENT ID | DEPART-MENT NAME | ELECTRONIC MAIL ADDRESS | ... |
|---|---|---|---|---|---|---|---|
| ⋮ | ⋮ | ⋮ | ⋮ | ⋮ | ⋮ | ⋮ | ⋮ |

| INDIVIDUAL (SAMPLE) NUMBER | AMINO ACID CONCENTRATION DATA | | | | | |
|---|---|---|---|---|---|---|
| | Gly | Leu | Val | Ile | Phe | ... |
| A-1 | 9.5 | 11.2 | 2.7 | 8.5 | 4.9 | ... |
| A-2 | 8.5 | 10.5 | 3.9 | 9.8 | 6.1 | ... |
| ⋮ | ⋮ | ⋮ | | | | |

| INDEX NUMBER | INDEX FORMULA |
|---|---|
| 1 | $\frac{Phe}{Val} + \frac{Thr+Met+Orn}{Pro+Gly}$ |
| ⋮ | |

| INDIVIDUAL (SAMPLE) NUMBER | INDEX NUMBER | INDEX VALUE |
|---|---|---|
| A-1 | 1 | 1.13 |
| ⋮ | ⋮ | |

| INDIVIDUAL (SAMPLE) NUMBER | INDEX VALUE | EVALUATION RESULT |
|---|---|---|
| A-1 | 1.13 | |
| ⋮ | ⋮ | |

FIG.16

| CUTOFF VALUE | F0, 1, 2 vs F3, 4 | | | | F0, 1, 2, 3 vs F4 | | | |
|---|---|---|---|---|---|---|---|---|
| | SENSITIVITY | SPECIFICITY | POSITIVE PREDICTIVE VALUE | NEGATIVE PREDICTIVE VALUE | SENSITIVITY | SPECIFICITY | POSITIVE PREDICTIVE VALUE | NEGATIVE PREDICTIVE VALUE |
| 0.77 | 1.00 | 0.19 | 0.53 | 1.00 | 1.00 | 0.12 | 0.33 | 1.00 |
| 0.90 | 0.92 | 0.54 | 0.69 | 0.89 | 1.00 | 0.47 | 0.46 | 1.00 |
| 0.95 | 0.89 | 0.88 | 0.79 | 0.88 | 1.00 | 0.63 | 0.55 | 1.00 |
| 1.00 | 0.85 | 0.87 | 0.85 | 0.85 | 1.00 | 0.75 | 0.62 | 1.00 |
| 1.05 | 0.77 | 1.00 | 0.95 | 0.81 | 1.00 | 0.88 | 0.76 | 1.00 |
| 1.10 | 0.56 | 1.00 | 1.00 | 0.71 | 0.81 | 0.96 | 0.87 | 0.92 |
| 1.20 | 0.45 | 1.00 | 1.00 | 0.64 | 0.66 | 0.97 | 0.91 | 0.86 |
| 1.28 | 0.42 | 1.00 | 1.00 | 0.63 | 0.63 | 1.00 | 1.00 | 0.86 |

FIG.17

| | INDEX | F0, 1, 2 vs. F3, 4 | | | | F0, 1, 2, 3 vs. F4 | | | |
|---|---|---|---|---|---|---|---|---|---|
| | | SENSITIVITY | SPECIFICITY | AUC | ± STANDARD ERROR | SENSITIVITY | SPECIFICITY | AUC | ± STANDARD ERROR |
| 1 | (Met)/(Pro)+(Thr+Phe+Orn)/(Val+Ile) | 0.78 | 0.81 | 0.88 | 0.05 | 1.00 | 0.75 | 0.95 | 0.04 |
| 2 | (Met+Orn)/(Pro+Ile)+(Thr+Phe)/(Val) | 0.78 | 0.81 | 0.88 | 0.05 | 1.00 | 0.75 | 0.95 | 0.03 |
| 3 | (Met+Orn)/(Val)+(Phe)/(Pro) | 0.81 | 0.73 | 0.86 | 0.05 | 0.97 | 0.75 | 0.94 | 0.04 |
| 4 | (Met+Orn+Tyr)/(Pro+Gly+Leu) | 0.89 | 0.73 | 0.89 | 0.05 | 0.95 | 0.75 | 0.91 | 0.04 |
| 5 | (Orn)/(Pro+Gly)+(Thr+Phe)/(Val) | 0.93 | 0.73 | 0.89 | 0.05 | 1.00 | 0.75 | 0.95 | 0.03 |
| 6 | (Orn)/(Pro+Gly)+(Thr+Phe)/(Val+Ile) | 0.96 | 0.69 | 0.90 | 0.04 | 1.00 | 0.75 | 0.95 | 0.03 |
| 7 | (Orn)/(Pro+Ile)+(Thr+Met+Phe)/(Val) | 0.70 | 0.85 | 0.88 | 0.05 | 1.00 | 0.75 | 0.94 | 0.03 |
| 8 | (Phe)/(Pro)+(Thr+Met+Orn)/(Val) | 0.85 | 0.77 | 0.88 | 0.05 | 0.97 | 0.75 | 0.96 | 0.03 |
| 9 | (Phe)/(Val+Leu)+(Thr+Met+Orn)/(Pro+Gly) | 0.89 | 0.85 | 0.92 | 0.04 | 0.95 | 0.81 | 0.97 | 0.02 |
| 10 | (Phe+Orn)/(Pro+Gly+Val) | 0.81 | 0.81 | 0.85 | 0.05 | 0.95 | 0.75 | 0.90 | 0.06 |
| 11 | (Phe+Orn)/(Pro+Val) | 0.93 | 0.69 | 0.85 | 0.05 | 0.97 | 0.63 | 0.91 | 0.05 |
| 12 | (Phe+Orn)/(Val)+(Cys)/(Gly) | 0.89 | 0.73 | 0.84 | 0.06 | 1.00 | 0.69 | 0.92 | 0.05 |
| 13 | (Phe+Orn)/(Val)+(Thr+Met)/(Pro+Gly) | 0.85 | 0.77 | 0.90 | 0.04 | 1.00 | 0.69 | 0.95 | 0.03 |
| 14 | (Phe+Thr)/(Gly+Leu+Ile) | 0.85 | 0.81 | 0.91 | 0.04 | 0.84 | 0.88 | 0.93 | 0.03 |
| 15 | (Phe+Thr)/(Pro+Gly+Ile) | 0.93 | 0.65 | 0.86 | 0.05 | 0.92 | 0.81 | 0.91 | 0.05 |
| 16 | (Phe+Thr)/(Pro+Gly+Val+Ile) | 0.96 | 0.69 | 0.88 | 0.05 | 0.89 | 0.88 | 0.96 | 0.03 |
| 17 | (Phe+Thr)/(Pro+Gly+Val+Leu) | 0.96 | 0.69 | 0.88 | 0.05 | 0.89 | 0.94 | 0.96 | 0.02 |
| 18 | (Phe+Thr+Met)/(Gly+Val) | 0.96 | 0.69 | 0.87 | 0.05 | 0.86 | 0.88 | 0.94 | 0.03 |
| 19 | (Phe+Thr+Met+Orn)/(Pro+Gly+Ile) | 0.89 | 0.77 | 0.90 | 0.04 | 0.97 | 0.69 | 0.93 | 0.04 |
| 20 | (Phe+Thr+Met+Orn)/(Pro+Gly+Leu) | 0.81 | 0.85 | 0.91 | 0.04 | 0.95 | 0.75 | 0.94 | 0.03 |
| 21 | (Phe+Thr+Met+Orn+Tyr)/(Pro+Gly+Leu) | 0.96 | 0.77 | 0.91 | 0.04 | 0.97 | 0.81 | 0.95 | 0.03 |
| 22 | (Phe+Thr+Met+Tyr)/(Gly+Leu+Ile) | 0.93 | 0.81 | 0.91 | 0.04 | 0.89 | 0.81 | 0.93 | 0.04 |
| 23 | (Thr)/(Gly)+(Glu+Phe)/(Leu) | 0.89 | 0.77 | 0.93 | 0.03 | 0.92 | 0.75 | 0.94 | 0.03 |
| 24 | (Thr)/(Gly)+(Phe)/(Val) | 0.89 | 0.81 | 0.88 | 0.05 | 0.95 | 0.63 | 0.93 | 0.03 |
| 25 | (Thr)/(Val)+(Phe)/(Gly) | 0.96 | 0.65 | 0.88 | 0.05 | 0.95 | 0.69 | 0.95 | 0.03 |
| 26 | (Thr+Asn+Cys)/(Val+Lys)+(Phe+Orn)/(Pro+Gly) | 0.96 | 0.73 | 0.90 | 0.05 | 1.00 | 0.81 | 0.99 | 0.01 |
| 27 | (Thr+Asn+Met+Orn)/(Pro+Gly)+(Phe)/(Val) | 0.96 | 0.77 | 0.92 | 0.04 | 0.92 | 0.94 | 0.98 | 0.01 |
| 28 | (Thr+Asn+Phe)/(Val+Lys)+(Cys+Orn)/(Pro+Gly) | 0.93 | 0.73 | 0.89 | 0.05 | 1.00 | 0.81 | 0.98 | 0.02 |
| 29 | (Thr+Cys+Met)/(Val+Lys)+(Phe+Orn)/(Pro+Gly) | 0.96 | 0.73 | 0.90 | 0.05 | 0.92 | 0.94 | 0.99 | 0.01 |
| 30 | (Thr+Cys+Phe)/(Gly+Val) | 0.81 | 0.77 | 0.85 | 0.05 | 0.92 | 0.75 | 0.94 | 0.03 |
| 31 | (Thr+Glu+Phe)/(Gly+Val) | 0.93 | 0.77 | 0.89 | 0.05 | 0.97 | 0.63 | 0.93 | 0.04 |
| 32 | (Thr+Met+Orn)/(Pro+Gly)+(Asn+Phe)/(Val+His) | 1.00 | 0.77 | 0.92 | 0.04 | 0.95 | 0.88 | 0.98 | 0.01 |
| 33 | (Thr+Met+Orn)/(Pro+Gly+His)+(Phe)/(Aba+Val) | 0.81 | 0.88 | 0.92 | 0.04 | 0.97 | 0.88 | 0.98 | 0.01 |
| 34 | (Thr+Met+Orn)/(Val+Lys)+(Cys+Phe)/(Pro+Gly) | 0.85 | 0.77 | 0.88 | 0.05 | 1.00 | 0.81 | 0.98 | 0.02 |
| 35 | (Thr+Orn)/(Val+Lys)+(Cys+Met+Phe)/(Pro+Gly) | 0.93 | 0.73 | 0.89 | 0.05 | 0.95 | 0.88 | 0.98 | 0.01 |
| 36 | (Thr+Orn+Tyr)/(Gly+Val) | 0.85 | 0.81 | 0.90 | 0.04 | 0.89 | 0.81 | 0.91 | 0.04 |
| 37 | (Thr+Phe)/(Gly+Val) | 0.89 | 0.73 | 0.87 | 0.05 | 0.95 | 0.63 | 0.93 | 0.03 |
| 38 | (Phe)/(Val)+(Thr+Met+Orn)/(Pro+Gly) | 0.96 | 0.77 | 0.92 | 0.04 | 0.95 | 0.94 | 0.99 | 0.03 |
| 39 | (Phe)/(Val)+(Thr+Orn)/(Pro+Gly) | 0.85 | 0.85 | 0.92 | 0.05 | 0.97 | 0.81 | 0.98 | 0.03 |
| 40 | (Phe)/(Val)+(Thr)/(Pro+Gly) | 1.00 | 0.65 | 0.88 | 0.04 | 0.95 | 0.88 | 0.97 | 0.03 |

FIG.18

| | INDEX | F0, 1, 2 vs. F3, 4 | | | | F0, 1, 2, 3 vs. F4 | | | |
|---|---|---|---|---|---|---|---|---|---|
| | | SENSITIVITY | SPECIFICITY | AUC | ± STANDARD ERROR | SENSITIVITY | SPECIFICITY | AUC | ± STANDARD ERROR |
| 41 | (Phe)/(Leu)+(Thr+Met+Orn)/(Pro+Gly) | 0.93 | 0.77 | 0.93 | 0.04 | 0.97 | 0.75 | 0.97 | 0.03 |
| 42 | (Phe)/(Leu)+(Thr+Met)/(Gly) | 0.93 | 0.81 | 0.91 | 0.05 | 0.92 | 0.81 | 0.95 | 0.03 |
| 43 | (Phe)/(Val)+(Thr+Met)/(Pro+Gly) | 0.89 | 0.77 | 0.88 | 0.04 | 0.92 | 0.88 | 0.97 | 0.03 |
| 44 | (Phe)/(Val)+(Met+Orn)/(Pro+Gly) | 0.85 | 0.81 | 0.89 | 0.04 | 0.92 | 0.88 | 0.94 | 0.03 |
| 45 | (Phe)/(Leu)+(Thr+Met)/(Pro+Gly) | 1.00 | 0.65 | 0.90 | 0.05 | 0.92 | 0.88 | 0.96 | 0.03 |
| 46 | (Phe)/(Leu)+(Thr+Orn)/(Pro+Gly) | 0.85 | 0.81 | 0.93 | 0.04 | 0.97 | 0.75 | 0.96 | 0.03 |
| 47 | (Phe)/(Leu)+(Thr)/(Gly) | 0.85 | 0.85 | 0.92 | 0.04 | 0.92 | 0.81 | 0.95 | 0.03 |
| 48 | (Phe)/(Ile)+(Thr+Met+Orn)/(Pro+Gly) | 0.70 | 0.92 | 0.90 | 0.05 | 0.97 | 0.75 | 0.95 | 0.03 |
| 49 | (Phe)/(Ile)+(Thr+Orn)/(Pro+Gly) | 0.70 | 0.92 | 0.90 | 0.04 | 0.97 | 0.75 | 0.96 | 0.03 |
| 50 | (Phe)/(Ile)+(Met+Orn)/(Gly) | 0.89 | 0.85 | 0.91 | 0.05 | 0.86 | 0.81 | 0.94 | 0.03 |
| 51 | (Phe)/(Ile)+(Orn)/(Gly) | 0.85 | 0.85 | 0.90 | 0.05 | 1.00 | 0.56 | 0.94 | 0.03 |
| 52 | (Phe)/(Ile)+(Thr+Met+Orn)/(Gly) | 0.81 | 0.85 | 0.92 | 0.04 | 0.86 | 0.88 | 0.95 | 0.03 |
| 53 | (Phe)/(Ile)+(Thr+Met)/(Gly) | 0.81 | 0.85 | 0.91 | 0.05 | 0.84 | 0.94 | 0.96 | 0.04 |
| 54 | (Phe)/(Ile)+(Thr+Orn)/(Gly) | 0.81 | 0.85 | 0.91 | 0.05 | 0.86 | 0.88 | 0.95 | 0.04 |
| 55 | (Phe)/(Ile)+(Thr)/(Pro+Gly) | 0.81 | 0.85 | 0.89 | 0.05 | 0.97 | 0.63 | 0.93 | 0.04 |
| 56 | (Phe)/(Ile)+(Met)/(Pro+Gly) | 0.81 | 0.85 | 0.87 | 0.05 | 0.97 | 0.63 | 0.92 | 0.03 |
| 57 | (Phe)/(Ile)+(Met)/(Gly) | 0.81 | 0.85 | 0.87 | 0.05 | 0.97 | 0.63 | 0.93 | 0.03 |
| 58 | (Phe)/(Ile)+(Orn)/(Pro) | 0.74 | 0.92 | 0.87 | 0.05 | 1.00 | 0.56 | 0.93 | 0.03 |
| 59 | (Phe)/(Val)+(Thr+Met)/(Gly) | 0.89 | 0.81 | 0.89 | 0.04 | 0.84 | 0.88 | 0.93 | 0.01 |
| 60 | (Phe)/(Val)+(Thr)/(Gly) | 0.89 | 0.81 | 0.88 | 0.06 | 0.95 | 0.63 | 0.93 | 0.04 |
| 61 | (Phe)/(Val)+(Orn)/(Pro+Gly) | 0.81 | 0.81 | 0.88 | 0.05 | 0.92 | 0.81 | 0.93 | 0.04 |
| 62 | (Phe)/(Leu)+(Thr)/(Pro+Gly) | 1.00 | 0.62 | 0.90 | 0.05 | 0.92 | 0.81 | 0.95 | 0.02 |
| 63 | (Phe)/(Leu)+(Met+Orn)/(Pro+Gly) | 0.81 | 0.85 | 0.92 | 0.06 | 0.84 | 0.94 | 0.96 | 0.04 |
| 64 | (Tyr)/(Ile)+(Thr+Met+Orn)/(Gly) | 0.93 | 0.73 | 0.91 | 0.05 | 0.92 | 0.75 | 0.91 | 0.03 |
| 65 | (Tyr)/(Ile)+(Thr+Orn)/(Gly) | 0.93 | 0.73 | 0.90 | 0.04 | 0.92 | 0.75 | 0.91 | 0.02 |
| 66 | (Tyr)/(Val)+(Thr+Met+Orn)/(Pro+Gly) | 0.85 | 0.81 | 0.91 | 0.06 | 0.89 | 0.81 | 0.94 | 0.05 |
| 67 | (Phe)/(Ile)+(Thr+Met)/(Pro+Gly) | 0.81 | 0.81 | 0.89 | 0.05 | 0.92 | 0.75 | 0.94 | 0.05 |
| 68 | (Phe)/(Ile)+(Thr)/(Gly) | 0.78 | 0.85 | 0.91 | 0.05 | 0.86 | 0.88 | 0.95 | 0.02 |
| 69 | (Phe)/(Ile)+(Met+Orn)/(Pro+Gly) | 0.78 | 0.88 | 0.89 | 0.06 | 0.86 | 0.81 | 0.94 | 0.04 |
| 70 | (Phe)/(Ile)+(Orn)/(Pro+Gly) | 0.78 | 0.88 | 0.88 | 0.05 | 0.86 | 0.81 | 0.93 | 0.03 |
| 71 | (Phe)/(Leu)+(Met+Orn)/(Pro) | 0.85 | 0.73 | 0.86 | 0.05 | 0.97 | 0.69 | 0.93 | 0.04 |
| 72 | (Phe)/(Leu)+(Orn)/(Pro+Gly) | 0.78 | 0.85 | 0.91 | 0.06 | 1.00 | 0.56 | 0.94 | 0.05 |
| 73 | (Tyr)/(Val)+(Thr+Met)/(Pro+Gly) | 0.89 | 0.73 | 0.87 | 0.05 | 0.97 | 0.63 | 0.92 | 0.05 |
| 74 | (Tyr)/(Val)+(Thr+Orn)/(Pro+Gly) | 0.81 | 0.85 | 0.90 | 0.06 | 0.86 | 0.81 | 0.94 | 0.04 |
| 75 | (Tyr)/(Val)+(Thr+Orn)/(Gly) | 0.89 | 0.81 | 0.89 | 0.06 | 0.81 | 0.88 | 0.89 | 0.04 |
| 76 | (Tyr)/(Val)+(Thr)/(Pro+Gly) | 0.89 | 0.73 | 0.87 | 0.05 | 0.97 | 0.63 | 0.92 | 0.03 |
| 77 | (Tyr)/(Val)+(Met+Orn)/(Pro+Gly) | 0.81 | 0.85 | 0.89 | 0.05 | 0.97 | 0.56 | 0.92 | 0.05 |
| 78 | (Tyr)/(Val)+(Orn)/(Pro+Gly) | 0.81 | 0.85 | 0.89 | 0.06 | 1.00 | 0.50 | 0.91 | 0.06 |
| 79 | (Tyr)/(Leu)+(Thr+Met)/(Gly) | 0.85 | 0.81 | 0.89 | 0.05 | 0.89 | 0.75 | 0.91 | 0.05 |
| 80 | (Tyr)/(Leu)+(Thr+Orn)/(Gly) | 0.93 | 0.73 | 0.91 | 0.04 | 0.86 | 0.81 | 0.91 | 0.02 |

FIG.19

| | INDEX | F0, 1, 2 vs. F3, 4 | | | | F0, 1, 2, 3 vs. F4 | | | |
|---|---|---|---|---|---|---|---|---|---|
| | | SENSITIVITY | SPECIFICITY | AUC | ± STANDARD ERROR | SENSITIVITY | SPECIFICITY | AUC | ± STANDARD ERROR |
| 81 | (Phe)/(Ile)+(Met+Orn)/(Pro) | 0.67 | 0.92 | 0.87 | 0.05 | 1.00 | 0.56 | 0.94 | 0.04 |
| 82 | (Phe)/(Val)+(Met+Orn)/(Gly) | 1.00 | 0.58 | 0.87 | 0.04 | 0.92 | 0.75 | 0.90 | 0.03 |
| 83 | (Phe)/(Val)+(Met)/(Pro+Gly) | 0.81 | 0.73 | 0.84 | 0.04 | 0.97 | 0.69 | 0.93 | 0.02 |
| 84 | (Phe)/(Val)+(Met)/(Gly) | 0.85 | 0.69 | 0.86 | 0.06 | 0.97 | 0.69 | 0.94 | 0.04 |
| 85 | (Phe)/(Leu)+(Thr+Met+Orn)/(Gly) | 0.70 | 0.92 | 0.91 | 0.04 | 0.84 | 0.88 | 0.93 | 0.03 |
| 86 | (Phe)/(Leu)+(Thr+Orn)/(Gly) | 0.93 | 0.69 | 0.90 | 0.03 | 0.84 | 0.88 | 0.92 | 0.02 |
| 87 | (Phe)/(Leu)+(Orn)/(Pro) | 0.85 | 0.73 | 0.86 | 0.05 | 0.95 | 0.69 | 0.92 | 0.04 |
| 88 | (Phe)/(Leu)+(Orn)/(Gly) | 0.70 | 0.88 | 0.89 | 0.04 | 0.92 | 0.75 | 0.92 | 0.04 |
| 89 | (Tyr)/(Ile)+(Thr)/(Gly) | 0.78 | 0.88 | 0.89 | 0.04 | 0.86 | 0.75 | 0.90 | 0.03 |
| 90 | (Tyr)/(Val)+(Thr+Met+Orn)/(Gly) | 0.89 | 0.77 | 0.89 | 0.05 | 0.84 | 0.81 | 0.90 | 0.04 |
| 91 | (Tyr)/(Val)+(Thr)/(Gly) | 0.85 | 0.81 | 0.88 | 0.04 | 0.92 | 0.63 | 0.90 | 0.03 |
| 92 | (Tyr)/(Leu)+(Thr+Met+Orn)/(Gly) | 0.78 | 0.85 | 0.91 | 0.04 | 0.86 | 0.81 | 0.92 | 0.02 |
| 93 | (Tyr)/(Leu)+(Thr+Met)/(Pro+Gly) | 0.85 | 0.77 | 0.89 | 0.05 | 0.95 | 0.63 | 0.91 | 0.04 |
| 94 | (Tyr)/(Leu)+(Thr)/(Pro+Gly) | 0.70 | 0.92 | 0.89 | 0.04 | 0.95 | 0.63 | 0.90 | 0.04 |
| 95 | (Tyr)/(Leu)+(Thr)/(Gly) | 0.85 | 0.81 | 0.90 | 0.05 | 0.86 | 0.75 | 0.90 | 0.04 |
| 96 | (Tyr)/(Leu)+(Met+Orn)/(Pro+Gly) | 0.74 | 0.88 | 0.90 | 0.05 | 0.92 | 0.69 | 0.91 | 0.04 |
| 97 | (Tyr)/(Leu)+(Orn)/(Pro+Gly) | 0.70 | 0.92 | 0.91 | 0.05 | 0.92 | 0.69 | 0.91 | 0.03 |
| 98 | (Phe)/(Ile)+(Thr+Met)/(Pro) | 0.93 | 0.62 | 0.85 | 0.04 | 0.89 | 0.81 | 0.93 | 0.03 |
| 99 | (Phe)/(Val)+(Met+Orn)/(Pro) | 0.78 | 0.73 | 0.82 | 0.05 | 0.97 | 0.69 | 0.91 | 0.04 |
| 100 | (Phe)/(Leu)+(Thr)/(Pro) | 0.93 | 0.62 | 0.84 | 0.04 | 0.89 | 0.81 | 0.92 | 0.04 |
| 101 | (Phe)/(Leu)+(Met+Orn)/(Gly) | 0.93 | 0.65 | 0.89 | 0.04 | 0.92 | 0.69 | 0.92 | 0.04 |
| 102 | (Phe)/(Leu)+(Met)/(Pro+Gly) | 0.70 | 0.85 | 0.87 | 0.05 | 0.97 | 0.63 | 0.93 | 0.05 |
| 103 | (Phe)/(Leu)+(Met)/(Gly) | 0.70 | 0.88 | 0.88 | 0.04 | 0.86 | 0.81 | 0.93 | 0.04 |
| 104 | (Tyr)/(Ile)+(Thr+Met)/(Pro) | 0.63 | 0.92 | 0.86 | 0.05 | 0.95 | 0.69 | 0.90 | 0.04 |
| 105 | (Tyr)/(Ile)+(Thr+Met)/(Gly) | 0.74 | 0.88 | 0.89 | 0.05 | 0.86 | 0.75 | 0.90 | 0.05 |
| 106 | (Tyr)/(Ile)+(Thr+Orn)/(Pro+Gly) | 0.70 | 0.92 | 0.90 | 0.04 | 0.89 | 0.69 | 0.91 | 0.05 |
| 107 | (Tyr)/(Ile)+(Thr)/(Pro) | 0.85 | 0.69 | 0.87 | 0.04 | 0.95 | 0.69 | 0.90 | 0.04 |
| 108 | (Tyr)/(Ile)+(Met+Orn)/(Pro+Gly) | 0.70 | 0.92 | 0.89 | 0.05 | 0.97 | 0.50 | 0.91 | 0.04 |
| 109 | (Tyr)/(Ile)+(Met+Orn)/(Pro) | 0.63 | 0.96 | 0.88 | 0.04 | 0.95 | 0.63 | 0.90 | 0.04 |
| 110 | (Tyr)/(Ile)+(Met+Orn)/(Gly) | 0.89 | 0.73 | 0.90 | 0.05 | 0.86 | 0.75 | 0.91 | 0.04 |
| 111 | (Tyr)/(Ile)+(Met)/(Gly) | 0.74 | 0.88 | 0.87 | 0.05 | 1.00 | 0.44 | 0.89 | 0.05 |
| 112 | (Tyr)/(Ile)+(Orn)/(Pro+Gly) | 0.81 | 0.81 | 0.89 | 0.04 | 1.00 | 0.44 | 0.90 | 0.05 |
| 113 | (Tyr)/(Ile)+(Orn)/(Gly) | 0.74 | 0.88 | 0.89 | 0.04 | 1.00 | 0.44 | 0.90 | 0.04 |
| 114 | (Tyr)/(Val)+(Thr+Met)/(Gly) | 0.89 | 0.77 | 0.87 | 0.05 | 0.84 | 0.75 | 0.90 | 0.04 |
| 115 | (Tyr)/(Val)+(Met+Orn)/(Pro) | 0.81 | 0.69 | 0.83 | 0.04 | 1.00 | 0.63 | 0.90 | 0.04 |
| 116 | (Tyr)/(Leu)+(Thr+Met+Orn)/(Pro+Gly) | 0.63 | 0.96 | 0.91 | 0.05 | 0.89 | 0.75 | 0.92 | 0.05 |
| 117 | (Tyr)/(Leu)+(Thr+Orn)/(Pro+Gly) | 0.63 | 0.96 | 0.91 | 0.05 | 0.89 | 0.75 | 0.92 | 0.05 |
| 118 | (Tyr)/(Leu)+(Met+Orn)/(Gly) | 0.85 | 0.77 | 0.90 | 0.05 | 0.84 | 0.81 | 0.91 | 0.05 |
| 119 | (Tyr)/(Leu)+(Met)/(Pro+Gly) | 0.74 | 0.88 | 0.88 | 0.04 | 0.95 | 0.56 | 0.88 | 0.04 |
| 120 | (Tyr)/(Leu)+(Met)/(Gly) | 0.74 | 0.88 | 0.89 | 0.05 | 0.92 | 0.63 | 0.89 | 0.04 |

FIG.20

| | INDEX | F0, 1, 2 vs. F3, 4 | | | | F0, 1, 2, 3 vs. F4 | | | |
|---|---|---|---|---|---|---|---|---|---|
| | | SENSITIVITY | SPECIFICITY | AUC | ± STANDARD ERROR | SENSITIVITY | SPECIFICITY | AUC | ± STANDARD ERROR |
| 121 | (Tyr)/(Leu)+(Orn)/(Pro) | 0.59 | 0.96 | 0.87 | 0.04 | 1.00 | 0.56 | 0.90 | 0.04 |
| 122 | (Phe)/(Ile)+(Thr+Met+Orn)/(Pro) | 0.85 | 0.69 | 0.85 | 0.04 | 0.92 | 0.69 | 0.93 | 0.03 |
| 123 | (Phe)/(Ile)+(Thr)/(Pro) | 0.93 | 0.62 | 0.85 | 0.06 | 0.86 | 0.81 | 0.93 | 0.05 |
| 124 | (Phe)/(Ile)+(Met)/(Pro) | 0.81 | 0.73 | 0.85 | 0.05 | 0.97 | 0.56 | 0.92 | 0.04 |
| 125 | (Phe)/(Val)+(Orn)/(Gly) | 1.00 | 0.54 | 0.86 | 0.05 | 0.92 | 0.69 | 0.88 | 0.04 |
| 126 | (Phe)/(Leu)+(Thr+Met)/(Pro) | 0.89 | 0.62 | 0.83 | 0.06 | 0.89 | 0.81 | 0.92 | 0.05 |
| 127 | (Tyr)/(Ile)+(Thr+Met+Orn)/(Pro+Gly) | 0.67 | 0.92 | 0.90 | 0.05 | 0.89 | 0.69 | 0.91 | 0.04 |
| 128 | (Tyr)/(Ile)+(Thr+Met)/(Pro+Gly) | 0.70 | 0.88 | 0.88 | 0.04 | 0.89 | 0.69 | 0.91 | 0.03 |
| 129 | (Tyr)/(Ile)+(Thr)/(Pro+Gly) | 0.70 | 0.88 | 0.88 | 0.06 | 0.89 | 0.69 | 0.90 | 0.05 |
| 130 | (Tyr)/(Ile)+(Met)/(Pro+Gly) | 0.70 | 0.88 | 0.86 | 0.05 | 1.00 | 0.44 | 0.89 | 0.04 |
| 131 | (Tyr)/(Ile)+(Orn)/(Pro) | 0.67 | 0.92 | 0.88 | 0.05 | 0.95 | 0.56 | 0.90 | 0.04 |
| 132 | (Tyr)/(Val)+(Met+Orn)/(Gly) | 0.78 | 0.81 | 0.88 | 0.06 | 0.92 | 0.63 | 0.90 | 0.05 |
| 133 | (Tyr)/(Leu)+(Thr+Met)/(Pro) | 0.89 | 0.65 | 0.84 | 0.05 | 0.95 | 0.63 | 0.90 | 0.04 |
| 134 | (Tyr)/(Leu)+(Met+Orn)/(Pro) | 0.67 | 0.88 | 0.87 | 0.04 | 0.97 | 0.56 | 0.91 | 0.04 |
| 135 | (Tyr)/(Leu)+(Met)/(Pro) | 0.70 | 0.88 | 0.87 | 0.06 | 0.92 | 0.63 | 0.90 | 0.05 |
| 136 | (Phe)/(Val)+(Thr+Met)/(Pro) | 0.89 | 0.62 | 0.79 | 0.05 | 0.89 | 0.75 | 0.91 | 0.04 |
| 137 | (Phe)/(Val)+(Orn)/(Pro) | 0.74 | 0.77 | 0.81 | 0.05 | 0.95 | 0.63 | 0.87 | 0.04 |
| 138 | (Phe)/(Leu)+(Thr+Met+Orn)/(Pro) | 0.81 | 0.69 | 0.83 | 0.05 | 1.00 | 0.50 | 0.92 | 0.04 |
| 139 | (Phe)/(Leu)+(Thr+Orn)/(Pro) | 0.74 | 0.77 | 0.83 | 0.05 | 1.00 | 0.50 | 0.91 | 0.04 |
| 140 | (Phe)/(Leu)+(Met)/(Pro) | 0.67 | 0.85 | 0.87 | 0.05 | 0.89 | 0.75 | 0.93 | 0.04 |
| 141 | (Tyr)/(Ile)+(Thr+Orn)/(Pro) | 0.78 | 0.77 | 0.87 | 0.05 | 0.86 | 0.75 | 0.91 | 0.05 |
| 142 | (Tyr)/(Ile)+(Met)/(Pro) | 0.70 | 0.88 | 0.86 | 0.05 | 0.89 | 0.63 | 0.89 | 0.05 |
| 143 | (Tyr)/(Val)+(Met)/(Pro) | 0.81 | 0.69 | 0.84 | 0.04 | 0.92 | 0.69 | 0.90 | 0.04 |
| 144 | (Tyr)/(Val)+(Met)/(Gly) | 0.74 | 0.85 | 0.86 | 0.05 | 0.84 | 0.75 | 0.90 | 0.05 |
| 145 | (Tyr)/(Val)+(Orn)/(Pro) | 0.78 | 0.73 | 0.84 | 0.04 | 0.95 | 0.63 | 0.88 | 0.04 |
| 146 | (Tyr)/(Val)+(Orn)/(Gly) | 0.85 | 0.73 | 0.88 | 0.04 | 0.84 | 0.75 | 0.88 | 0.04 |
| 147 | (Tyr)/(Leu)+(Thr+Met+Orn)/(Pro) | 0.78 | 0.73 | 0.85 | 0.05 | 1.00 | 0.50 | 0.90 | 0.05 |
| 148 | (Tyr)/(Leu)+(Thr+Orn)/(Pro) | 0.67 | 0.85 | 0.85 | 0.05 | 1.00 | 0.50 | 0.90 | 0.04 |
| 149 | (Tyr)/(Leu)+(Thr)/(Pro) | 0.81 | 0.69 | 0.85 | 0.04 | 0.95 | 0.63 | 0.90 | 0.04 |
| 150 | (Phe)/(Val)+(Met)/(Pro) | 0.78 | 0.69 | 0.80 | 0.05 | 0.97 | 0.63 | 0.92 | 0.05 |
| 151 | (Phe)/(Ile)+(Thr+Orn)/(Pro) | 0.59 | 0.92 | 0.85 | 0.04 | 0.81 | 0.88 | 0.93 | 0.04 |
| 152 | (Phe)/(Val)+(Thr+Met+Orn)/(Gly) | 0.67 | 0.88 | 0.88 | 0.04 | 0.81 | 0.81 | 0.90 | 0.04 |
| 153 | (Phe)/(Val)+(Thr+Orn)/(Gly) | 0.89 | 0.65 | 0.87 | 0.05 | 0.81 | 0.81 | 0.88 | 0.05 |
| 154 | (Tyr)/(Ile)+(Thr+Met+Orn)/(Pro) | 0.56 | 0.96 | 0.86 | 0.04 | 0.86 | 0.75 | 0.90 | 0.04 |
| 155 | (Tyr)/(Val)+(Met)/(Pro+Gly) | 0.74 | 0.81 | 0.85 | 0.04 | 0.81 | 0.75 | 0.89 | 0.04 |
| 156 | (Phe)/(Val)+(Thr)/(Pro) | 0.93 | 0.54 | 0.80 | 0.05 | 0.89 | 0.69 | 0.91 | 0.04 |
| 157 | (Tyr)/(Val)+(Thr+Met+Orn)/(Pro) | 0.78 | 0.69 | 0.81 | 0.04 | 0.97 | 0.50 | 0.89 | 0.04 |
| 158 | (Tyr)/(Val)+(Thr+Met)/(Pro) | 0.89 | 0.58 | 0.80 | 0.05 | 0.86 | 0.75 | 0.89 | 0.05 |
| 159 | (Tyr)/(Val)+(Thr+Orn)/(Pro) | 0.78 | 0.69 | 0.81 | 0.05 | 1.00 | 0.44 | 0.88 | 0.05 |
| 160 | (Tyr)/(Val)+(Thr)/(Pro) | 0.89 | 0.58 | 0.81 | 0.05 | 0.95 | 0.56 | 0.89 | 0.05 |
| 161 | (Phe)/(Val)+(Thr+Met+Orn)/(Pro) | 0.81 | 0.69 | 0.80 | 0.04 | 0.76 | 0.88 | 0.89 | 0.04 |
| 162 | (Phe)/(Val)+(Thr+Orn)/(Pro) | 0.81 | 0.65 | 0.78 | 0.05 | 0.92 | 0.56 | 0.87 | 0.04 |

HEPATIC DISEASE-EVALUATING APPARATUS, HEPATIC DISEASE-EVALUATING METHOD, HEPATIC DISEASE-EVALUATING SYSTEM, HEPATIC DISEASE-EVALUATING PROGRAM AND RECORDING MEDIUM

This application is a continuation of International Application No. PCT/JP2006/310164, filed May 22, 2006, which claims the benefit of Japanese Application No. 2005-157802, filed May 30, 2005; and is also a continuation-in-part of application Ser. No. 11/148,352, filed Jun. 9, 2005, which is a continuation of International Application No. PCT/JP2003/015713, filed Dec. 9, 2003, which claims the benefit of Japanese Application No. 2002-357042, filed Dec. 9, 2002 and Japanese Application No. 2003-205589, filed Aug. 1, 2003.

BACKGROUND OF THE INVENTION

1. Field of the Invention

The present invention relates to a hepatic disease-evaluating apparatus, a hepatic disease-evaluating method, a hepatic disease-evaluating system, and a hepatic disease-evaluating program and recording medium that calculate an index indicating the degree of hepatic fibrosis from amino acid concentration data to be evaluated based on an index formula and evaluate the disease state of the hepatic disease to be evaluated based on the index value.

2. Description of the Related Art

Hepatic biopsy and laparoscopy have been used mainly for diagnosis of the progress of hepatic fibrosis and also of liver cirrhosis. The score by the METAVIR scoring method consisting of five progressive stages (F0, F1, F2, F3, and F4) has been used as the indicator of the progress of hepatic fibrosis. Here, the stage F0 indicates that there is no hepatic fibrosis, and the stages F1, F2, F3 and F4 indicate that there is the hepatic fibrosis. Hepatic fibrosis starts in the stage F1, progresses gradually to the stages F2 and F3, and reaches liver cirrhosis in the stage F4.

However, these traditional diagnostic methods are invasive, giving the patient physical and mental burdens such as pain, and thus are accompanied with risks such as bleeding during test.

For that reason, methods of diagnosing progress of hepatic fibrosis and liver cirrhosis by using one blood component or a combination of two or more blood components such as platelet, globulin, AST (aspartate aminotransferase), ALT (alanine aminotransferase), albumin, and hyaluronic acid as an index have been proposed recently as the non-invasive diagnostic methods (see U.S. patent application Ser. No. 09/687,459 and "Luo J. C., Hwang S. J., Chang F. Y., Chu C. W., Lai C. R., Wang Y. J., Lee P. C., Tsay S. H., and Lee S. D., "Simple blood tests can predict compensated liver cirrhosis in patients with chronic hepatitis C", Hepatogastroenterology, 49, 478, 2002", "Pohl A., Behling C., Oliver D., Kilani M., Monson P., and Hassanein T., "Serum aminotransferase levels and platelet counts as predictors of degree of fibrosis in chronic hepatitis C virus infection", Am. J. Gastroenterol, 96, 3142, 2001", and "Wai C. T., Greenson J. K., Fontana R. J., Kalbfleisch J. D., Marrero J. A., Conjeevaram H. S., and Lok A. S., "A simple noninvasive index can predict both significant fibrosis and cirrhosis in patients with chronic hepatitis C", Hepatology, 38, 518, 2003").

In addition, the Fischer ratio "(Leu+Val+Ile)+(Phe+Tyr)" based on blood amino acid concentration (see "J. E. Fischer, J. M. Funovics, A. Aguirre, J. H. James, J. M. Keane, R. I. Wesdorp, N. Yoshimura, and T. Westman, "The role of plasma amino acids in hepatic encephalopathy", Surgery, 78, 276-290, 1975") or the BTR (branched-chain amino acids and tyrosine ratio) ratio, which is a simplified Fischer ratio, "(Leu+Val+Ile)÷Tyr" is used for diagnosis of hepatic encephalopathy in the patient with liver cirrhosis, as an index for use in clinical diagnosis of hepatic disease.

In addition, the index employed in the hepatic fibrosis analyzer described in WO 2004/052,191 is also used for evaluation of hepatitis, and it is possible to determine whether a patient is with hepatitis or not from blood amino acid concentration by using the index.

Clinically, there is a need for an index aimed at determining whether treatment with interferon/ribavirin combination (intervention with the treatment) is needed to a patient with a hepatic disease. In particular, there is a need for an index for determining whether the hepatic fibrosis of a patient is in the stage of F0, F1, or F2 or in the stage of F3 or F4 and an index for determining whether the hepatic fibrosis of a patient is in the stage of F0, F1, F2, or F3 or in the stage of F4.

However because the conventional methods did not always permit accurate evaluation of the progress of the disease state of hepatic diseases, it was not always possible to determine whether treatment is needed after test, depending on the disease state to be diagnosed. For example, there is currently no non-invasive index that can determine whether treatment with interferon/ribavirin combination is needed to the patients with a hepatic disease with sufficiently high accuracy, and thus, it was not possible to determine whether the treatment is needed to the patient with sufficiently high accuracy with conventional indices.

SUMMARY OF THE INVENTION

It is an object of the present invention to at least partially solve the problems in the conventional technology.

For example, an object of the present invention, which was made to solve the problems above, is to provide a hepatic disease-evaluating apparatus, a hepatic disease-evaluating method, a hepatic disease-evaluating system, and a hepatic disease-evaluating program and a recording medium carrying the same that allow accurate evaluation of the progress of the disease state of hepatic disease and accurate determination, for example, of whether treatment with interferon/ribavirin combination is needed to patients with a hepatic disease.

To solve the above problems and achieve the above objects, a hepatic disease-evaluating apparatus, a hepatic disease-evaluating method, and a hepatic disease-evaluating program which making a computer execute a hepatic disease-evaluating method according to one aspect of the present invention, include an index calculating unit (index calculating step) that calculates (of calculating) an index indicating the degree of hepatic fibrosis from the amino acid concentration data to be evaluated including amino acid concentration value, based on one or more indices of fractional expression having amino acid concentration as variable, and a disease state evaluating unit (disease state evaluating step) that evaluates (of evaluating) the disease state of the hepatic disease to be evaluated, based on the index calculated by (at) the index calculating unit (index calculating step), wherein the index has a numerator of the fractional expression including at least one of Phe and Tyr and at least one of Thr, Met and Orn and a denominator of the fractional expression including at least one of Val, Leu and Ile and at least one of Pro and Gly, or the numerator of the fractional expression including at least one of Val, Leu and Ile and at least one of Pro and Gly and the denominator of the fractional expression including at least one of Phe and Tyr and at least one of Thr, Met and Orn.

Another aspect of the present invention is the hepatic disease-evaluating apparatus, the hepatic disease-evaluating method, and the hepatic disease-evaluating program, wherein the index is the sum of two fractional expressions; the numerator in one fractional expression is any one of Phe and Tyr and the denominator in the one fractional expression is any one of Val, Leu, and Ile; and the numerator in the other fractional expression is the sum of at least one of Thr, Met and Orn and the denominator of the other fractional expression is the sum of at least one of Pro and Gly.

Still another aspect of the present invention is the hepatic disease-evaluating apparatus, the hepatic disease-evaluating method, and the hepatic disease-evaluating program, wherein the index is the sum of the two fractional expressions; the numerator in the one fractional expression is Phe and the denominator in the one fractional expression is Val; and the numerator in the other fractional expression is the sum of Thr, Met and Orn and the denominator of the other fractional expression is the sum of Pro and Gly.

Still another aspect of the present invention is the hepatic disease-evaluating apparatus, the hepatic disease-evaluating method, and the hepatic disease-evaluating program, wherein the hepatic disease includes at least one of hepatitis, chronic hepatitis, hepatic fibrosis and liver cirrhosis.

The present invention also relates to a hepatic disease-evaluating system, and the hepatic disease-evaluating system according to one aspect of the present invention includes a hepatic disease-evaluating apparatus that evaluates hepatic disease and a information communication terminal apparatus that provides the amino acid concentration data to be evaluated including amino acid concentration value that are connected to each other communicatively via a network, wherein the information communication terminal apparatus includes a sending unit that sends the amino acid concentration data to be evaluated to the hepatic disease-evaluating apparatus and a receiving unit that receives the evaluation results of the disease state of the hepatic disease to be evaluated sent from the hepatic disease-evaluating apparatus, the hepatic disease-evaluating apparatus includes a receiving unit that receives the amino acid concentration data to be evaluated sent from the information communication terminal apparatus, an index calculating unit that calculates an index indicating the degree of hepatic fibrosis from the amino acid concentration data to be evaluated received by the receiving unit, based on one or more indices of fractional expression having amino acid concentration as variable, a disease state evaluating unit that evaluates the disease state of the hepatic disease to be evaluated, based on the index calculated by the index calculating unit, and a sending unit that sends the evaluation results obtained by the disease state evaluating unit to the information communication terminal apparatus, wherein the index has a numerator of the fractional expression including at least one of Phe and Tyr and at least one of Thr, Met and Orn and a denominator of the fractional expression including at least one of Val, Leu and Ile and at least one of Pro and Gly, or the numerator of the fractional expression including at least one of Val, Leu and Ile and at least one of Pro and Gly and the denominator of the fractional expression including at least one of Phe and Tyr and at least one of Thr, Met and Orn.

Another aspect of the present invention is the hepatic disease-evaluating system, wherein the index is the sum of two fractional expressions; the numerator in one fractional expression is any one of Phe and Tyr and the denominator in the one fractional expression is any one of Val, Leu, and Ile; and the numerator in the other fractional expression is the sum of at least one of Thr, Met and Orn and the denominator of the other fractional expression is the sum of at least one of Pro and Gly.

Still another aspect of the present invention is the hepatic disease-evaluating system, wherein the index is the sum of the two fractional expressions; the numerator in the one fractional expression is Phe and the denominator in the one fractional expression is Val; and the numerator in the other fractional expression is the sum of Thr, Met and Orn and the denominator of the other fractional expression is the sum of Pro and Gly.

Still another aspect of the present invention is the hepatic disease-evaluating system, wherein the hepatic disease includes at least one of hepatitis, chronic hepatitis, hepatic fibrosis and liver cirrhosis.

The present invention also relates to a recording medium, and the recording medium according to one aspect of the present invention includes the hepatic disease-evaluating program described above.

The hepatic disease-evaluating apparatus, the hepatic disease-evaluating method and the hepatic disease-evaluating program according to the present invention, calculate the index indicating the degree of hepatic fibrosis from the amino acid concentration data to be evaluated including the value of amino acid (specifically, blood amino acid) concentration, based on one or more indices (one index or combination of plurality of indices) of fractional expression having amino acid concentration as variable, and evaluate the disease state of the hepatic disease to be evaluated based on the index value. The index formula used in calculation of the index has the numerator of the fractional expression including at least one of Phe and Tyr and at least one of Thr, Met and Orn and the denominator of the fractional expression including at least one of Val, Leu and Ile and at least one of Pro and Gly, or the numerator of the fractional expression including at least one of Val, Leu and Ile and at least one of Pro and Gly and the denominator of the fractional expression including at least one of Phe and Tyr and at least one of Thr, Met and Orn. In particular according to the present invention, it is possible to evaluate progress of the disease state of hepatic disease accurately and to determine, for example, whether treatment with interferon/ribavirin combination is needed to patients with a hepatic disease accurately. Specifically, it is possible to determine whether the hepatic fibrosis of a patient is in the stage of F0, F1, or F2 or in the stage of F3 or F4 accurately. Specifically, it is also possible to determine whether the hepatic fibrosis of a patient is in the stage of F0, F1, F2 or F3 or in the stage of F4 accurately.

In the hepatic disease-evaluating apparatus, the hepatic disease-evaluating method and the hepatic disease-evaluating program according to the present invention, the index is the sum of the two fractional expressions; the numerator in the one fractional expression is any one of Phe and Tyr and the denominator in the one fractional expression is any one of Val, Leu, and Ile; and the numerator in the other fractional expression is the sum of at least one of Thr, Met and Orn and the denominator of the other fractional expression is the sum of at least one of Pro and Gly. In particular according to the present invention, it is possible to evaluate progress of the disease state of hepatic disease more accurately and to determine, for example, whether treatment with interferon/ribavirin combination is needed to patients with a hepatic disease more accurately. Specifically, it is possible to determine whether the hepatic fibrosis of a patient is in the stage of F0, F1, or F2 or in the stage of F3 or F4 more accurately. Specifically, it is also possible to determine whether the hepatic fibrosis of a patient is in the stage of F0, F1, F2 or F3 or in the stage of F4 more accurately.

In the hepatic disease-evaluating apparatus, the hepatic disease-evaluating method and the hepatic disease-evaluating program according to the present invention, the index is the sum of the two fractional expressions; the numerator in the one fractional expression is Phe and the denominator in the one fractional expression is Val; and the numerator in the other fractional expression is the sum of Thr, Met and Orn and the denominator of the other fractional expression is the sum of Pro and Gly. In particular according to the present invention, it is possible to evaluate progress of the disease state of hepatic disease more accurately and to determine, for example, whether treatment with interferon/ribavirin combination is needed to patients with a hepatic disease more accurately. Specifically, it is possible to determine whether the hepatic fibrosis of a patient is in the stage of F0, F1, or F2 or in the stage of F3 or F4 more accurately. Specifically, it is also possible to determine whether the hepatic fibrosis of a patient is in the stage of F0, F1, F2 or F3 or in the stage of F4 more accurately.

In the hepatic disease-evaluating apparatus, the hepatic disease-evaluating method and the hepatic disease-evaluating program according to the present invention, the hepatic disease includes at least one of hepatitis, chronic hepatitis, hepatic fibrosis and liver cirrhosis, and thus, it, is possible to apply the present invention appropriately for clinically, frequently required evaluation of the disease state of at least one of diseases such as hepatitis, chronic hepatitis, hepatic fibrosis and liver cirrhosis.

In the hepatic disease-evaluating system according to the present invention, the information communication terminal apparatus sends the amino acid concentration data to be evaluated including the value concerning amino acid (specifically, blood amino acid) concentration to the hepatic disease-evaluating apparatus and receives the transmitted evaluation results concerning the disease state of the hepatic disease to be evaluated from the hepatic disease-evaluating apparatus; and the hepatic disease-evaluating apparatus receives the transmitted amino acid concentration data to be evaluated from the information communication terminal apparatus, calculates the index indicating the degree of the hepatic fibrosis from the received amino acid concentration data to be evaluated, based on one or more indices (one index or combination of plurality of indices) of fractional expression having amino acid concentration as variable, evaluates the disease state of the hepatic disease to be evaluated, based on the index value, and sends the evaluated evaluation results to the information communication terminal apparatus. The index used in the calculation of the index has the numerator of the fractional expression including at least one of Phe and Tyr and at least one of Thr, Met and Orn and the denominator of the fractional expression including at least one of Val, Leu and Ile and at least one of Pro and Gly, or the numerator of the fractional expression including at least one of Val, Leu and Ile and at least one of Pro and Gly and the denominator of the fractional expression including at least one of Phe and Try and at least one of Thr, Met and Orn. In particular according to the present invention, it is possible to evaluate progress of the disease state of hepatic disease accurately and to determine, for example, whether treatment with interferon/ribavirin combination is needed to patients with a hepatic disease accurately. Specifically, it is possible to determine whether the hepatic fibrosis of a patient is in the stage of F0, F1, or F2 or in the stage of F3 or F4 accurately. Specifically, it is also possible to determine whether the hepatic fibrosis of a patient is in the stage of F0, F1, F2 or F3 or in the stage of F4 accurately.

In the hepatic disease-evaluating system according to the present invention, the index is the sum of the two fractional expressions; the numerator in the one fractional expression is any one of Phe and Tyr and the denominator in the one fractional expression is any one of Val, Leu, and Ile; and the numerator in the other fractional expression is the sum of at least one of Thr, Met and Orn and the denominator of the other fractional expression is the sum of at least one of Pro and Gly. It is thus possible to evaluate progress of the disease state of hepatic disease more accurately and to determine, for example, whether treatment with interferon/ribavirin combination is needed to patients with a hepatic disease more accurately. Specifically, it is possible to determine whether the hepatic fibrosis of a patient is in the stage of F0, F1, or F2 or in the stage of F3 or F4 more accurately. Specifically, it is also possible to determine whether the hepatic fibrosis of a patient is in the stage of F0, F1, F2 or F3 or in the stage of F4 more accurately.

In the hepatic disease-evaluating system according to the present invention, the index is the sum of the two fractional expressions; the numerator in the one fractional expression is Phe and the denominator in the one fractional expression is Val; and the numerator in the other fractional expression is the sum of Thr, Met and Orn and the denominator of the other fractional expression is the sum of Pro and Gly. It is thus possible to evaluate progress of the disease state of hepatic disease more accurately and to determine, for example, whether treatment with interferon/ribavirin n combination is needed to patients with a hepatic disease more accurately. Specifically, it is possible to determine whether the hepatic fibrosis of a patient is in the stage of F0, F1, or F2 or in the stage of F3 or F4 more accurately. Specifically, it is also possible to determine whether the hepatic fibrosis of a patient is in the stage of F0, F1, F2 or F3 or in the stage of F4 more accurately.

In the hepatic disease-evaluating system according to the present invention, the hepatic disease includes at least one of hepatitis, chronic hepatitis, hepatic fibrosis and liver cirrhosis, and thus, it is possible to apply the present invention appropriately for clinically, frequently required evaluation of the disease state of at least one of diseases such as hepatitis, chronic hepatitis, hepatic fibrosis and liver cirrhosis.

In the recording medium according to the present invention, by making a computer read and execute the hepatic disease-evaluating program recorded on the recording medium and making the computer perform the hepatic disease-evaluating program, it is possible to obtain advantageous effects similar to those obtained by the hepatic disease-evaluating program.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a chart showing an example of the information stored in the user information file 106*a;*

FIG. 6 is a chart showing an example of the information stored in the amino acid concentration data file 106*b;*

FIG. 7 is a chart showing an example of the information stored in the index database 106*c;*

FIG. 16 is a chart showing the sensitivity, specificity, positive predictive value, and negative predictive value corresponding to each cutoff value in discrimination of two groups "F0, F1, or F2" and "F3 or F4", or two groups "F0, F1, F2, or F3" and "F4", by using the index 1;

FIG. 17 is a chart showing the sensitivity and the specificity corresponding to the optimal cutoff value in discrimination of two groups "F0, F1, or F2" and "F3 or F4", or two groups "F0, F1, F2, or F3" and "F4", by using an index almost similar in diagnostic performance (discrimination efficiency) to the index 1;

FIG. 18 is a chart showing the sensitivity and the specificity corresponding to the optimal cutoff value in discrimination of two groups "F0, F1, or F2" and "F3 or F4", or two groups "F0, F1, F2, or F3" and "F4", by using an index almost similar in diagnostic performance (discrimination efficiency) to the index 1;

FIG. 19 is a chart showing the sensitivity and the specificity corresponding to the optimal cutoff value in discrimination of two groups "F0, F1, or F2" and "F3 or F4", or two groups "F0, F1, F2, or F3" and "F4", by using an index almost similar in diagnostic performance (discrimination efficiency) to the index 1; and FIG. 20 is a chart showing the sensitivity and the specificity corresponding to the optimal cutoff value in discrimination of two groups "F0, F1, or F2" and "F3 or F4", or two groups "F0, F1, F2, or F3" and "F4", by using an index almost similar in diagnostic performance (discrimination efficiency) to the index 1.

DETAILED DESCRIPTION OF THE PREFERRED EMBODIMENTS

Hereinafter, embodiments of the hepatic disease-evaluating apparatus, the hepatic disease-evaluating method, the hepatic disease-evaluating system, the hepatic disease-evaluating program and the recording medium according to the present invention will be described in detail with reference to drawings. However, the present invention is not limited to these embodiments.

[1. Summary of the Present Invention]

Figure 1:
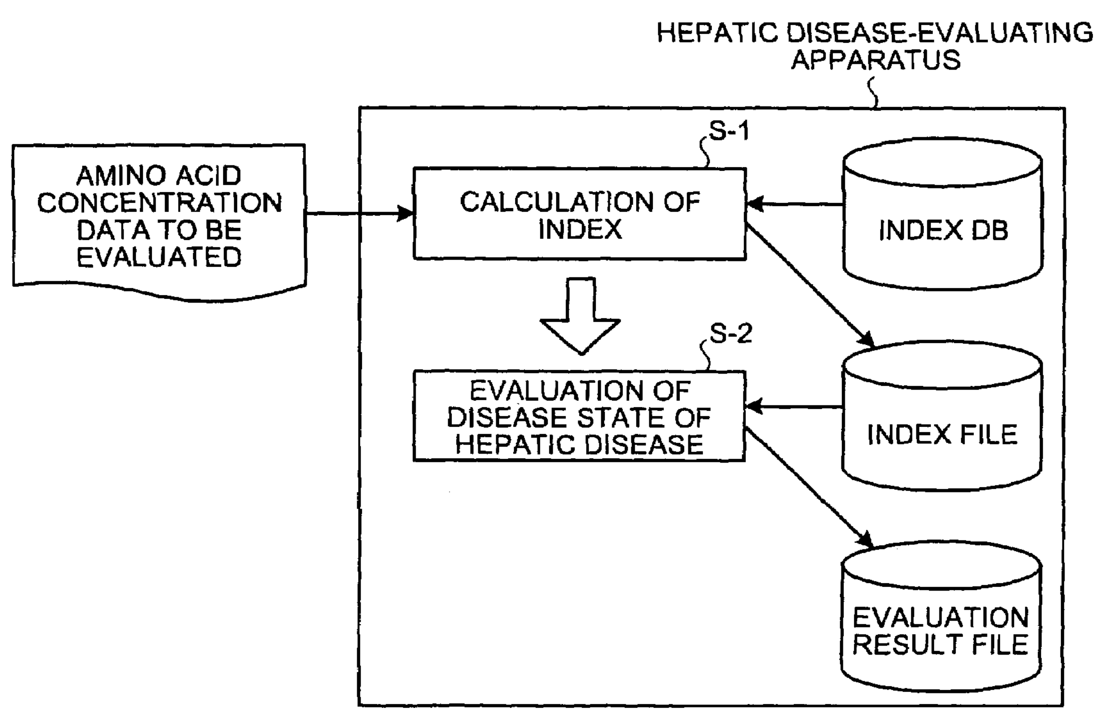
FIG. 1 is a principle configurational diagram showing the basic principle of the present invention.

The summary of the present invention will be described with reference to FIG. 1. FIG. 1 is a principle configurational diagram showing the basic principle of the present invention.

First, an index of the degree of hepatic fibrosis is calculated from previously obtained amino acid concentration data to be evaluated including amino acid concentration values, based on one or more indices (one index or combination of plurality of indices) (step S-1). In other words, the index is obtained by assigning the amino acid concentration values, based on the one or more indices. Data such as defective values and outliers may be removed from the amino acid concentration data before calculation of the index (data filtering or data editing).

The index used in step S-1 has a numerator of its fractional expressions including at least one of Phe and Tyr and at least one of Thr, Met and Orn and a denominator of the fractional expressions including at least one of Val, Leu and Ile and at least one of Pro and Gly, or the numerator of the fractional expressions including at least one of Val, Leu and Ile and at least one of Pro and Gly and the denominator of the fractional expressions including at least one of Phe and Tyr and at least one of Thr, Met and Orn. The index used in step S-1 is a index newly generated by taking clinical need into consideration, and aimed, in particular, at discriminating two groups "F0, F1, or F2" and "F3 or F4" or two groups "F0, F1, F2, or F3" and "F4" in the progressive stages of hepatic fibrosis.

The index used in step S-1 may be specifically the sum of two fractional expressions; the numerator in one fractional expression is any one of Phe and Tyr and the denominator in the one fractional expression is any one of Val, Leu, and Ile; and the numerator in the other fractional expression is the sum of at least one of Thr, Met and Orn, and the denominator of the other fractional expression is the sum of at least one of Pro and Gly. The index used in step S-1 in particular, may be the sum of the two fractional expressions, and the numerator in the one fractional expression may be Phe; the denominator in the one fractional expression, Val; the numerator in the other fractional expression, the sum of Thr, Met and Orn; and the denominator of the other fractional expression, the sum of Pro and Gly.

An amino acid having smaller influence on the sum of Phe and Tyr, the sum of Thr, Met, and Orn, the sum of Val, Leu, and Ile, or the sum of Pro and Gly may be added as the variable in the index used in step S-1. The phrase "having smaller influence" means that addition of the amino acid does not deteriorate the determination (discrimination) efficiency of the index.

The index used in step S-1 is obtained by the method described in International Publication WO 2004/052,191 filed by the present applicant. Hereinafter, the method will be described briefly. First obtained are fractional expressions optimizing discrimination of a target disease, by using a calculation method of optimizing the correlation of the targeted variable to be examined with the fractional expression having amino acid concentration as the variable. The fractional expression includes a divided fractional expression. Among the fractional expressions optimizing discrimination of the target disease, a fractional expression higher in diagnostic performance is selected as the diagnosis index.

Subsequently, the disease state of the hepatic disease to be evaluated is evaluated (predicted), based on the index calculated in step S-1 (step S-2). In other words, the disease state of the hepatic disease to be evaluated is evaluated (predicted) according to the index. Here in step S-2, it may be determined (discriminated) whether the disease state of the hepatic disease to be evaluated is in the progressive stage of hepatic fibrosis of F0, F1, or F2, or alternatively of F3 or F4, by comparing the index calculated in step S-1 with a previously set particular threshold value (cutoff value). It may also be determined (discriminated) whether the disease state of the hepatic disease to be evaluated is in the progressive stage of hepatic fibrosis of F0, F1, F2, or F3, or alternatively of F4, by comparing the index calculated in step S-1 with a previously set particular threshold value (cutoff value).

In the present invention, the hepatic diseases include at least one of hepatitis, chronic hepatitis, hepatic fibrosis and liver cirrhosis. The hepatitis is a hepatic disease causing hepatic dysfunction by hepatic inflammation, for example, due to infection of hepatitis virus (e.g., A, B, C, or D), excessive intake of alcohol, progress of fatty liver, or intake of medicine causing hepatopathy. Hepatitis includes that the hepatic inflammation is accompanied with diffuse or macular necrosis extending to the lobe. Hepatitis is induced by infection of hepatitis C virus at highest rate. Hepatitis advances gradually to chronic hepatitis. Alternatively, hepatic fibrosis is a biological reaction in response to the necrosis or damage of hepatic cell, and represents a state in which connective tissues are accumulated in the liver because of the unbalance between generation and decomposition of extracellular matrix. Hepatic fibrosis progresses further by decomposition of existing fiber and subsequent accumulation. Liver cirrhosis is a stage of advanced chronic hepatitis. In the liver of liver cirrhosis, there is observed, as pathologic change, diffuse structural decay of hepatic structure caused by regenerative nodules surrounded by fiber structure. Liver cirrhosis normally progresses irreversibly. Hereinafter, progress of hepatitis will be described, by taking hepatitis C virus (HCV) infection as an example. Hepatitis C is induced by infection of hepatitis C virus, specifically by infection of hepatitis C virus via body fluid. Hepatitis C becomes chronic at a high frequency (50% or more) and results in liver cirrhosis and consequently in hepatic cell cancer approximately 20 years after development of the symptom. Infection of hepatitis C virus results in constitutional malaise, and then causes symptoms such as anorexia, nausea, and vomiting. Infection of hepatitis C virus may also result in jaundice after these symptoms. Swelling of liver is occasionally observed as an objective symptom other than jaundice.

[2. System Configuration]

Hereinafter, the configuration of the hepatic disease-evaluating system according to the present invention (hereinafter, referred to as the present system) will be described with reference to FIGS. 2 to 11. First, the entire configuration of the present system will be described with reference to FIGS. 2 and 3.

Figure 2:
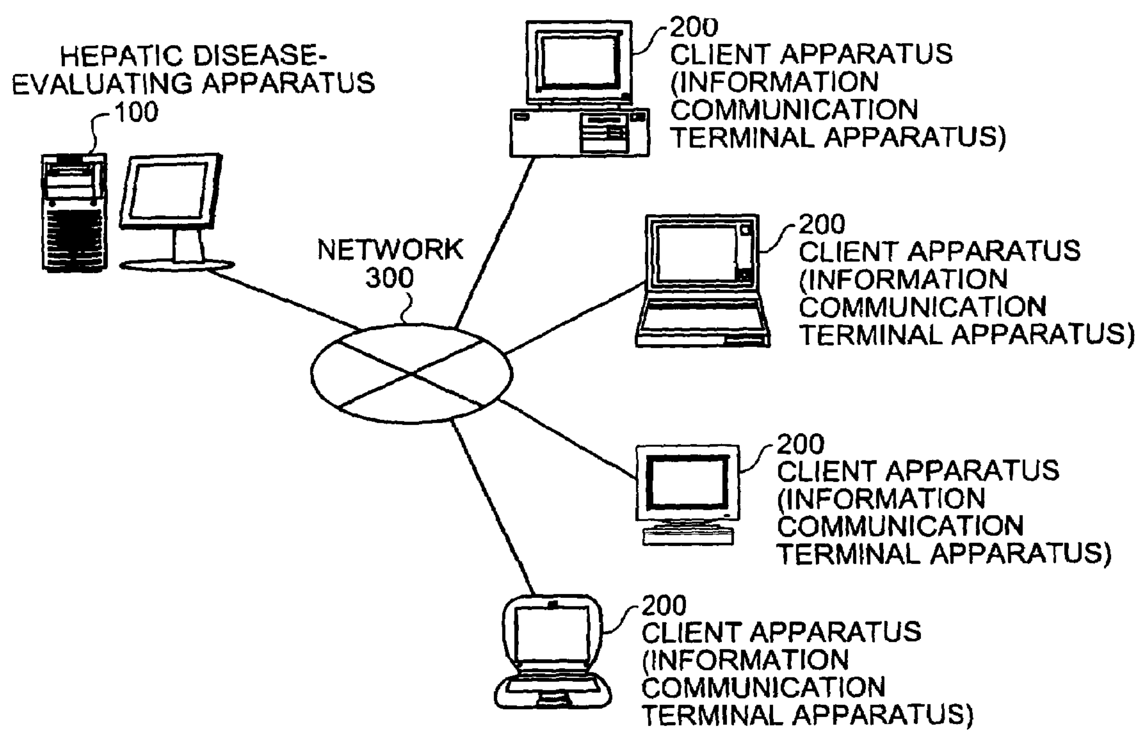
FIG. 2 is a diagram showing an example of the entire configuration of the present system.
Figure 3:
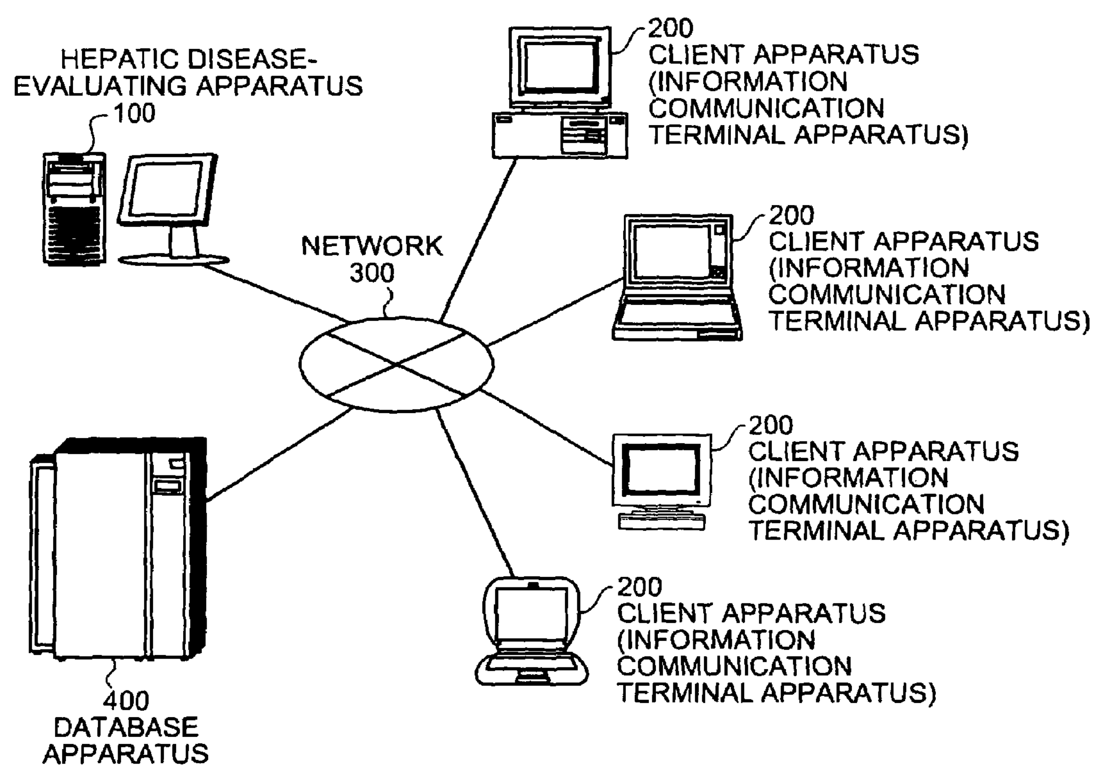
FIG. 3 is diagram showing another example of the entire configuration of the present system.

FIG. 2 is a diagram showing an example of the entire configuration of the present system. FIG. 3 is a diagram showing another example of the entire configuration of the present system.

As shown in FIG. 2, the present system includes a hepatic disease-evaluating apparatus 100 which evaluates hepatic disease and client apparatuses 200 as information communication terminal apparatuses which provide the amino acid concentration data to be evaluated that are communicatively connected to each other via a network 300. As shown in FIG. 3, in addition to the hepatic disease-evaluating apparatus 100 and the client apparatus 200, the present system may have a database apparatus 400 storing, for example, the amino acid concentration data transmitted from the client apparatuses 200, the index used in the hepatic disease-evaluating apparatus 100, and the evaluation results transmitted from the hepatic disease-evaluating apparatus 100 that is communicatively connected via the network 300. In this configuration, the evaluation results and others are provided via the network 300 from the hepatic disease-evaluating apparatus 100 to the client apparatuses 200 and the database apparatus 400, and the amino acid concentration data, index, and others are provided from the client apparatuses 200 and the database apparatus 400 to the hepatic disease-evaluating apparatus 100.

[2-1. System Configuration of Hepatic Disease-Evaluating Apparatus 100]

Figure 4:
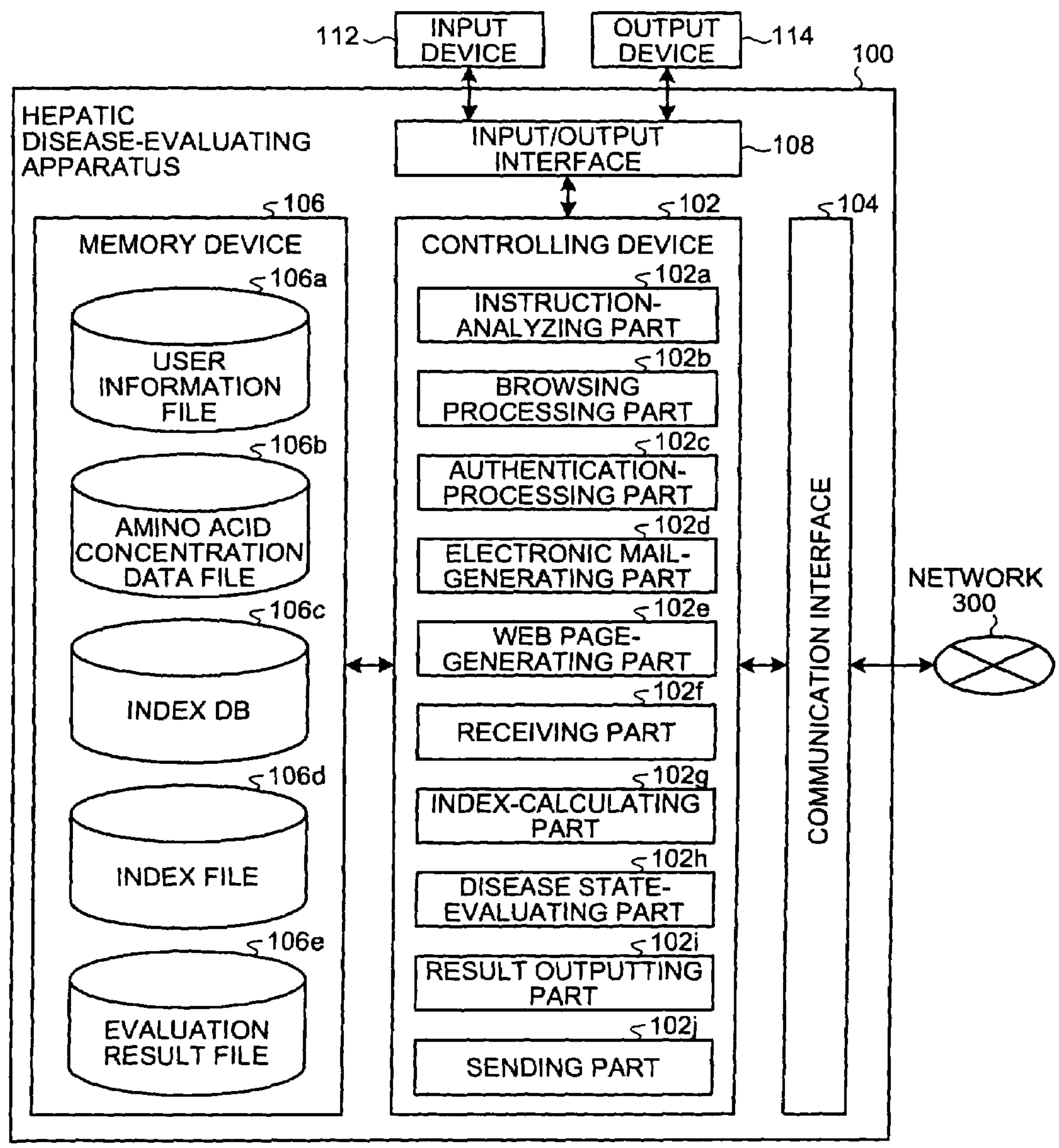
FIG. 4 is a block diagram showing an example of the configuration of the hepatic disease-evaluating apparatus 100 in the present system.

FIG. 4 is a block diagram showing an example of the configuration of the hepatic disease-evaluating apparatus 100 in the present system, showing conceptually only the region relevant to the present invention.

The hepatic disease-evaluating apparatus 100 includes a controlling device 102, such as CPU (Central Processing Unit), which integrally controls the hepatic disease-evaluating apparatus 100, a communication interface 104 which connects the hepatic disease-evaluating apparatus 100 to the network 300 communicatively via communication apparatuses such as router and a wired or wireless communication line such as private line, a memory device 106 storing various databases, tables, files and others, and an input/output interface 108 connected to an input device 112 and an output device 114, that are connected to each other communicatively via any communication channel. The hepatic disease-evaluating apparatus 100 may be present together with various analyzers (e.g., amino acid analyzer, etc.) in the same housing. Typical configuration of disintegration/integration of the hepatic disease-evaluating apparatus 100 is not limited to that shown in the figure, and all or part of it may be disintegrated or integrated functionally or physically in any unit, for example, according to various loads applied. For example, part of the processing may be performed via a CGI (Common Gateway Interface).

The memory device 106 is a storage means, and examples thereof include memory apparatuses such as RAM (Random Access Memory) and ROM (Read Only Memory), fixed disk drives such as hard disk, flexible disk, optical disk, and the like. The memory device 106 stores computer programs giving instructions to CPU for various processing, together with OS (Operating System). As shown in the figure, the memory device 106 stores a user information file 106*a*, an amino acid concentration data file 106*b*, an index database 106*c*, an index file 106*d*, and an evaluation result file 106*e*.

The user information file 106*a* stores information about users (user information). FIG. 5 is a chart showing an example of the information stored in the user information file 106*a*. As shown in FIG. 5, the information stored in the user information file 106*a* includes user ID (identification) for identifying the user uniquely, user password for authentication of the user, user name, organization ID uniquely identifying the organization of the user, department ID for uniquely identifying the department of the user organization, department name, and electronic mail address of the user that are correlated to each other.

Back in FIG. 4, the amino acid concentration data file 106*b* stores amino acid concentration data including amino acid concentration values. FIG. 6 is a chart showing an example of the information stored in the amino acid concentration data file 106*b*. As shown in FIG. 6, the information stored in the amino acid concentration data file 106*b* includes individual (sample) number and amino acid concentration data that are correlated to each other. In FIG. 6, the amino acid concentration data are assumed to be numerical values, i.e., on continuous scale, but the amino acid concentration data may be expressed on nominal scale or ordinal scale. In the case of nominal or ordinal scale, any number may be allocated to each state for analysis. The amino acid concentration data may be used in combination with other biological information (e.g., sex difference, age, smoking, digitalized electrocardiogram waveform, enzyme concentration, and gene expression quantity).

Back in FIG. 4, the index database 106*c* stores the indices used in the index-calculating part 102*g* described below. FIG. 7 is a chart showing an example of the information stored in the index database 106*c*. As shown in FIG. 7, the information stored in the index database 106*c* includes index number identifying each index uniquely and index of fractional expressions having amino acid concentrations as variables, that are correlated to each other.

Figure 8:
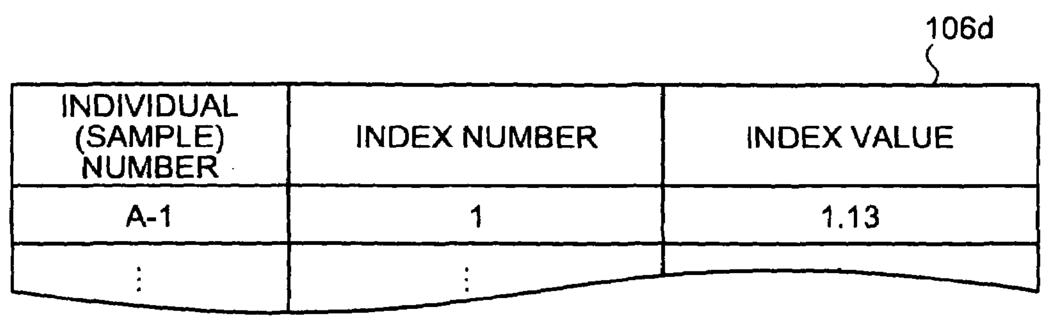
FIG. 8 is a chart showing an example of the information stored in the index file 106*d;*

Back in FIG. 4, the index file 106*d* stores the index indicating the degree of hepatic fibrosis calculated in the index-calculating part 102*g* described below. FIG. 8 is a chart showing an example of the information stored in the index file 106*d*. As shown in FIG. 8, the information stored in the index file 106*d* includes subject (sample) number of each subject to be evaluated, index number, and index value that are correlated to each other.

Figure 9:
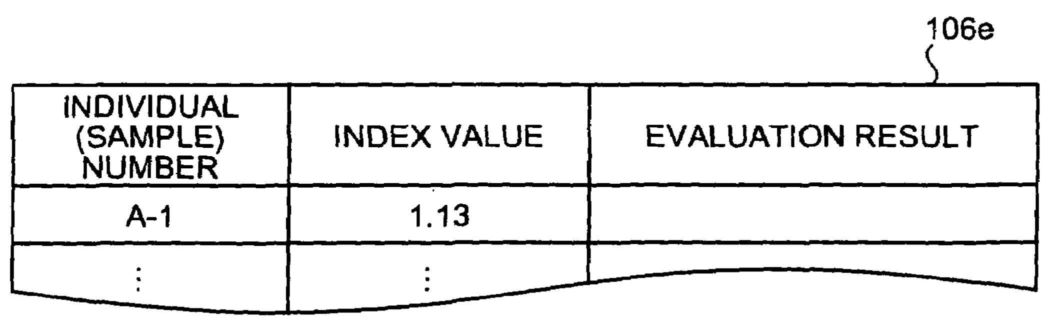
FIG. 9 is a chart showing an example of the information stored in the evaluation result file 106*e;*

Back in FIG. 4, the evaluation result file 106*e* stores the evaluation results obtained in the disease state-evaluating part 102*h* described below. FIG. 9 is a chart showing an example of the information stored in the evaluation result file 106*e*. The information stored in the evaluation result file 106*e* includes subject (sample) number of each subject to be evaluated, index value, and evaluation result (determination result, prediction result) that are correlated to each other.

Back in FIG. 4, in addition, the memory device 106 stores various Web data, CGI programs, and others for providing the client apparatuses 200 with web site information. The Web data include various data for displaying the Web page described below and others, and the data are generated as, for example, a HTML (HyperText Markup Language) or XML (Extensible Markup Language) text file. Other temporary files such as files for the components for generation of Web data and for operation, and others are also stored in the memory device 106. In addition, it may store as needed sound files in the WAVE or AIFF (Audio Interchange File Format) Format for transmission to the client apparatuses 200 and image files of still image or motion picture in the JPEG (Joint Photographic Experts Group) or MPEG2 (Moving Picture Experts Group phase 2) format.

The communication interface 104 allows communication between the hepatic disease-evaluating apparatus 100 and the network 300 (or communication apparatus such as router). Thus, the communication interface 104 has a function to communicate data via a communication line with other terminals.

The input/output interface 108 is connected to the input device 112 and the output device 114. A monitor (including home television), a speaker, or a printer may be used as the output device 114 (hereinafter, a monitor may be described as the output device 114). A keyboard, a mouse, a microphone, or a monitor functioning as a pointing device together with a mouse may be used as the input device 112.

The controlling device 102 has an internal memory storing control programs such as OS (Operating System), programs for various processing procedures, and other needed data, and performs information processing for execution of various processings according to these programs. As shown in the figure, the controlling device 102 includes mainly an instruction-analyzing part 102*a*, a browsing processing part 102*b*, an authentication-processing part 102*c*, an electronic mail-generating part 102*d*, a Web page-generating part 102*e*, a receiving part 102*f*, an index-calculating part 102*g*, a disease state-evaluating part 102*h*, a result outputting part 102*i*, and a sending part 102*j*. The controlling device 102 performs data processing (data filtering or data editing) such as removal of data including defective values or many outliers and of variables for the defective value-including data in the amino acid concentration data obtained in the receiving part 102*g* described below.

The instruction-analyzing part 102*a* analyzes the instruction from the client apparatus 200 or the database apparatus 400 and sends the instruction to other parts in the controlling device 102 according to the analytical result. Upon receiving browsing instruction for various screens from the client apparatus 200, the browsing processing part 102*b* generates and transmits the web data for these screens. Upon receiving authentication instruction from the client apparatus 200 or the database apparatus 400, the authentication-processing part 102*c* performs authentication. The electronic mail-generating part 102*d* generates an electronic mail including various information. The Web page-generating part 102*e* generates a Web page for user browsing.

The receiving part 102*f* receives the information (specifically, the amino acid concentration data including blood amino acid concentration values, and the indices) transmitted from the client apparatus 200 and the database apparatus 400. The index-calculating part 102*g* calculates the index indicating the degree of hepatic fibrosis from the amino acid concentration data to be evaluated received in the receiving part 102*f*, based on one or more indices (specifically, one or more indices stored in the index database 106*c*). Specifically, the index-calculating part 102*g* calculates the index by substituting the amino acid concentration data into one or more indices. The index-calculating part 102*g* may calculate the index from the amino acid concentration data, based on an index formula previously selected and downloaded from the indices stored in the memory device of the database apparatus 400.

The disease state-evaluating part 102*h* evaluates (predicts or determines) the disease state of the hepatic disease to be evaluated, based on the index calculated in the index-calculating part 102*g*. The disease state-evaluating part 102*h* may determine (discriminate) whether the progressive stage of hepatic fibrosis to be evaluated is in the stage of F0, F1, or F2, or in the stage of F3 or F4, by comparing the index with a previously set particular threshold value (cutoff value). Alternatively, the disease state-evaluating part 102*h* may determine (discriminate) whether the progressive stage of hepatic fibrosis to be evaluated is in the stage of F0, F1, F2, or F3 or in the stage of F4, by comparing the index with a previously set particular threshold value (cutoff value).

The result outputting part 102*i* outputs the evaluation results obtained in the disease state-evaluating part 102*h*, the processing results in the other processing parts, and others into the output device 114. The sending part 102*j* sends the evaluation results obtained in the disease state-evaluating part 102*h* to the client apparatus 200 that has sent the amino acid concentration data and the database apparatus 400 and other various information to the client apparatuses 200 and the database apparatus 400.

[2-2. System Configuration of Client Apparatus 200]

Figure 10:
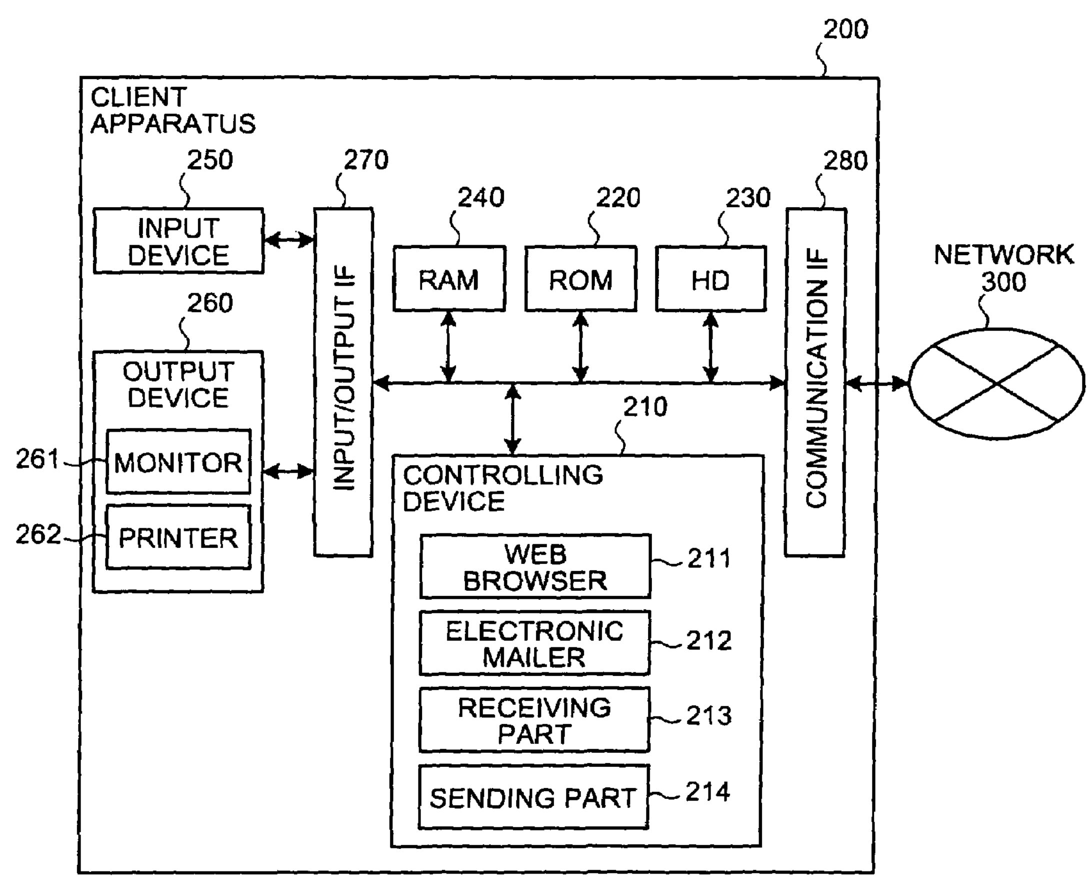
FIG. 10 is a block diagram showing an example of the configuration of the client apparatus 200 in the present system.

FIG. 10 is a block diagram showing an example of the configuration of the client apparatus 200 in the present system, showing conceptually only the region relevant to the present invention.

As shown in FIG. 10, the client apparatus 200 includes a controlling device 210, a ROM 220, a HD (Hard Disk) 230, a RAM 240, an input device 250, an output device 260, an input/output IF 270, and an communication IF 280 that are connected communicatively to each other. The controlling device 210 has a Web browser 211, an electronic mailer 212, a receiving part 213, and a sending part 214. The Web browser 211 performs browsing processing of interpreting Web data and displaying the interpreted Web data on a monitor 261 described below. The Web browser 211 may have various plug-in software, such as stream player, having functions to receive, display and feedback streaming screen image. The electronic-mailer 212 sends and receives electronic mails using a particular protocol (e.g., SMTP (Simple Mail Transfer Protocol) or POP3 (Post Office Protocol version 3)). The receiving part 213 receives various information, such as the evaluation results transmitted from the hepatic disease-evaluating apparatus 100, via the communication IF 280. The sending part 214 sends various information, such as the amino acid concentration data, to the hepatic disease-evaluating apparatus 100 and the database apparatus 400 via the communication IF 280. The input/output IF 270 is connected to the input device 250 and the output device 260. The input device 250 is, for example, a keyboard, mouse, or microphone. The monitor 261 described below also functions as a pointing device together with a mouse. The output device 260 is an output means for outputting the information received via the communication IF 280, and includes the monitor (including home television) 261 and a printer 262. In addition, the output device 260 may have a speaker or the like additionally. The communication IF 280 connects the client apparatus 200 to the network 300 (or communication apparatus such as router) communicatively. In other words, the client apparatuses 200 are connected to the network 300 via a communication apparatus such as modem, TA (Terminal Adapter) or router, and a telephone line, or a private line. In this way, the client apparatuses 200 can access to the hepatic disease-evaluating apparatus 100 and the database apparatus 400 by using a particular protocol.

The client apparatus 200 may be realized, as peripheral parts such as printer, monitor, and image scanner connected as needed to information processing apparatus (such as known personal computer, workstation, family computer, Internet TV (Television), or the other information processing terminal (such as PHS (Personal Handyphone System) terminal, mobile phone terminal, mobile unit communication terminal or PDA (Personal Digital Assistants))), and also as software (including programs, data and others) for Web data-browsing function and electronic mail-processing function installed in the information processing apparatus. All or part of the controlling device 210 in the client apparatus 200 may be performed by a CPU and programs read and executed by the CPU. Thus, computer programs for giving instructions to the CPU and executing various processings together with the OS (Operating System) are recorded in the ROM 220 or HD 230. The computer programs, which are executed as they are loaded in the RAM 240, constitute the controlling device 210 with the CPU. The computer programs may be stored in an application program server connected via any network to the client apparatus 200, and the client apparatus 200 may download all or part of them as needed. All or any part of the controlling device 210 may be substituted with hardware such as wired-logic.

[2-3. System Configuration of Network 300]

The network 300 has a function to connect the hepatic disease-evaluating apparatus 100, the client apparatuses 200, and the database apparatus 400 mutually, communicatively to each other, and is, for example, the Internet, intranet, or LAN (Local Area Network (both wired/wireless)). The network 300 may be VAN (Value Added Network), personal computer communication network, public telephone network (including both analog and digital), leased line network (including both analog and digital), CATV (Community Antenna Television) network, portable switched network or portable packet-switched network (including IMT2000 (International Mobile Telecommunication 2000) system, GSM (Global System for Mobile Communications) system, or PDC (Personal Digital Cellular)/PDC-P system), wireless calling network, local wireless network such as Bluetooth, PHS network, satellite communication network (including CS (Communication Satellite), BS (Broadcasting Satellite) and ISDB (Integrated Services Digital Broadcasting)), or the like.

[2-4. System Configuration of Database Apparatus 400]

Figure 11:
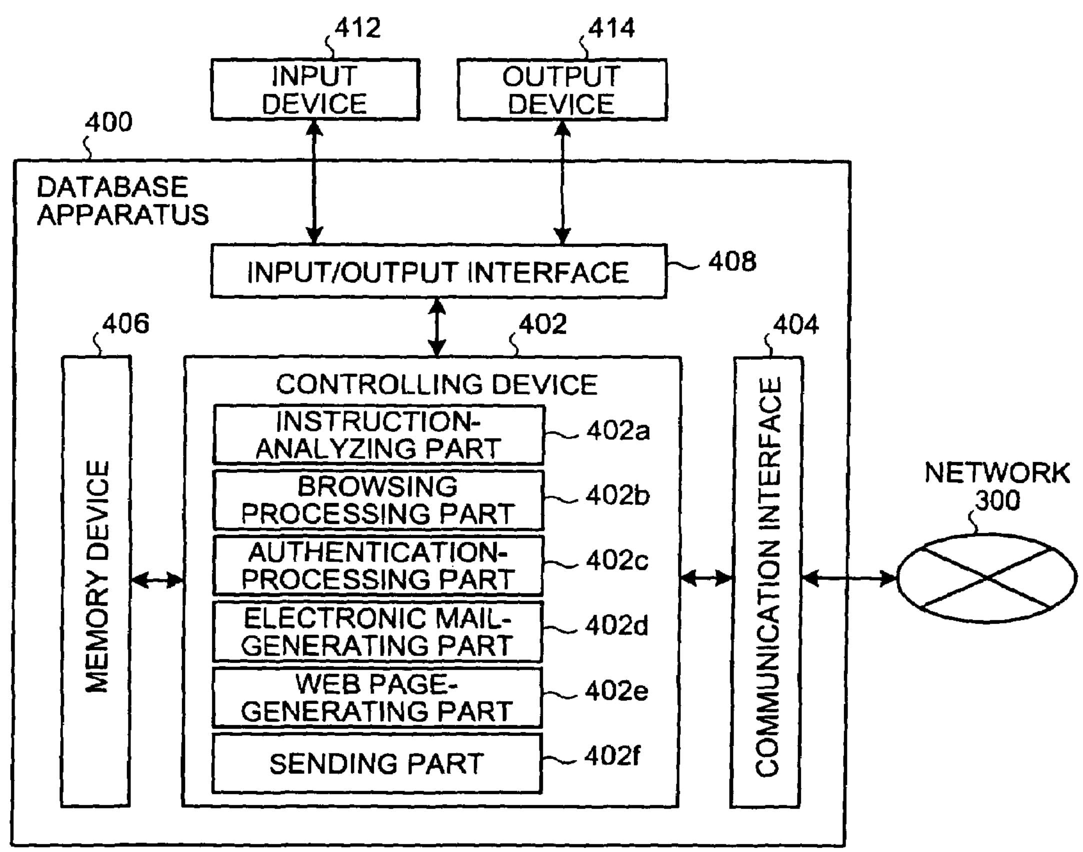
FIG. 11 is a block diagram showing an example of the configuration of the database apparatus 400 in the present system.

FIG. 11 is a block diagram showing an example of the configuration of the database apparatus 400 in the present system, showing conceptually only the region relevant to the present invention.

The database apparatus 400 has functions to store, for example, the amino acid concentration data to be evaluated transmitted from the client apparatuses 200, the indices used in the hepatic disease-evaluating apparatus 100, and the evaluation results obtained in the hepatic disease-evaluating apparatus 100. As shown in FIG. 11, the database apparatus 400 has mainly, a controlling device 402, such as CPU, which controls the entire database apparatus 400 integrally, a communication interface 404 connected to a communication apparatus such as router (not shown in the figure), for example, to a communication line, a memory device 406 storing various data, tables and others, and an input/output interface 408 connected to an input device 412 and an output device 414, and these parts are connected communicatively to each other via any communication channel. The database apparatus 400 is connected to the network 300 communicatively via a communication apparatus such as router and via a wired or wireless communication line such as private line.

The memory device 406 is a storage means, and may be, for example, memory apparatus such as RAM or ROM, fixed disk drive such as hard disk, flexible disk, optical disk, or the like. Various programs, tables, files, web-page files, and others used in various processings are stored in the memory device 406. The communication interface 404 allows communication between the database apparatus 400 and the network 300 (or communication apparatus such as router). Thus, the communication interface 404 has a function to communicate data with other terminal via a communication line. The input/output interface 408 is connected to the input device 412 and the output device 414. A monitor (including home television), a speaker, or a printer may be used as the output device 414 (hereinafter, a monitor may be described as the output device 414). A keyboard, a mouse, a microphone, or a monitor functioning as a pointing device together with a mouse may be used as the input device 412.

The controlling device 402 has an internal memory storing control programs such as OS (Operating System), programs for various processing procedures, and other needed data, and performs information processing for execution of various processings according to these programs. As shown in the figure, the controlling device 402 includes mainly an instruction-analyzing part 402*a*, a browsing processing part 402*b*, an authentication-processing part 402*c*, an electronic mail-generating part 402*d*, a Web page-generating part 402*e*, and a sending part 402*f*.

The instruction-analyzing part 402*a* analyzes the instruction from the hepatic disease-evaluating apparatus 100 and client apparatus 200 and sends the instruction to other parts in the controlling device 402 according to the analytical result.

Upon receiving various screen-browsing instructions from the hepatic disease-evaluating apparatus 100 and the client apparatus 200, the browsing processing part 402*b* generates and transmits web data for these screens. Upon receipt of authentication instruction from the hepatic disease-evaluating apparatus 100 or the client apparatus 200, the authentication-processing part 402*c* performs authentication. The electronic mail-generating part 402*d* generates an electronic mail including various information. The Web page-generating part 402*e* generates a Web page for user browsing. The sending part 402*f* sends the index to the hepatic disease-evaluating apparatus 100 and various information (e.g., the amino acid concentration data previously stored in a particular memory region of the memory device 406) to the hepatic disease-evaluating apparatus 100 and the client apparatuses 200.

[3. Processing in System]

Figure 12:
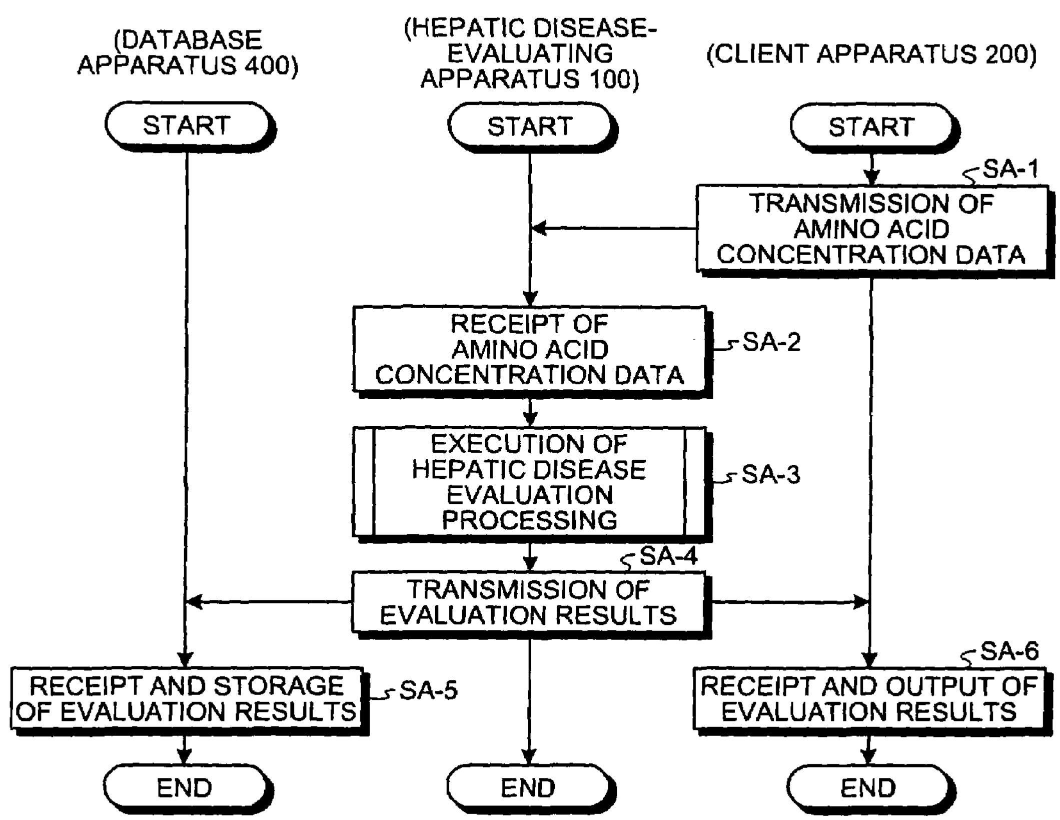
FIG. 12 is a flowchart showing an example of the hepatic disease evaluation service processing performed in the present system.
Figure 13:
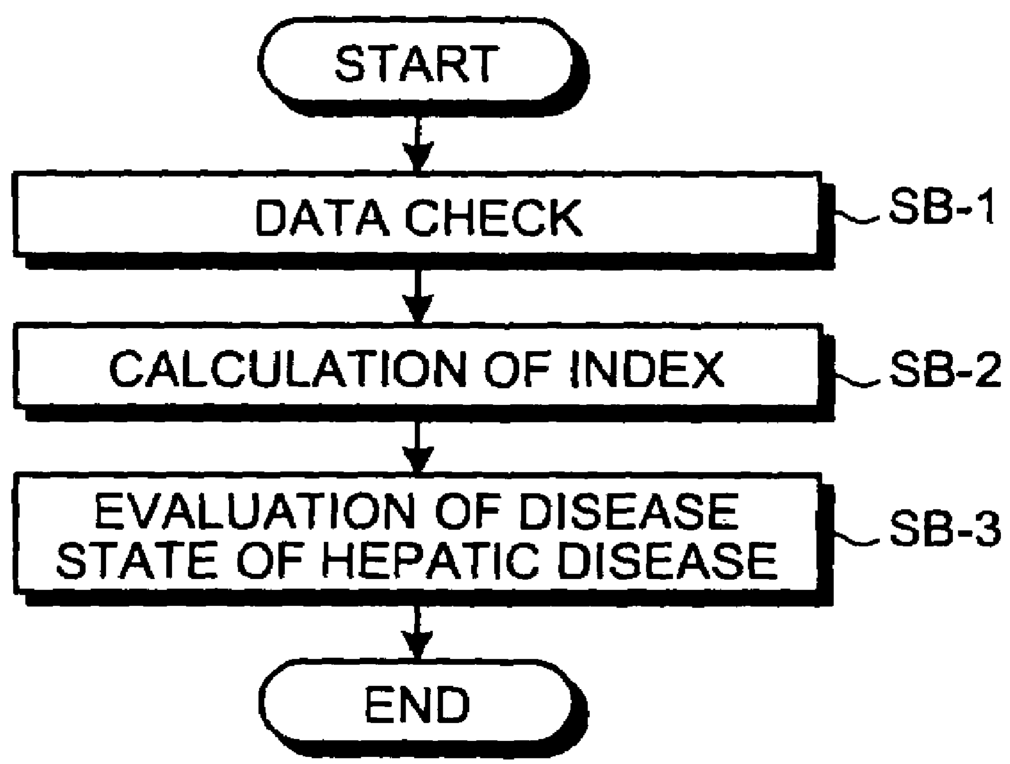
FIG. 13 is a flowchart showing an example of the hepatic disease evaluation processing performed in the hepatic disease-evaluating apparatus 100.

Hereinafter, an example of the processing performed in the present system in the configuration above will be described with reference to FIGS. 12 and 13.

[3-1. Hepatic Disease Evaluation Service Processing]

Here, an example of the hepatic disease evaluation service processing performed in the present system will be described with reference to FIG. 12. FIG. 12 is a flowchart showing an example of the hepatic disease evaluation service processing performed in the present system.

The amino acid concentration data to be evaluated used in the present processing is data including values concerning amino acid concentration obtained by analyzing blood previously collected from a subject to be evaluated. Hereinafter, the method of analyzing blood amino acid will be described briefly. First, a blood sample is collected in a heparin-treated tube, and then, the blood plasma is separated by centrifugation of the tube. All blood plasma sample separated is frozen and stored at minus 70° C. before measurement of amino acid concentration. Before measurement of amino acid concentration, to the blood plasma sample is added sulfosalicylic acid to a concentration of 3%, for removal of protein. An amino acid analyzer by high-performance liquid chromatography (HPLC) by using ninhydrin reaction in the post column was used for measurement of amino acid concentration.

First, the client apparatus 200 connects itself to the hepatic disease-evaluating apparatus 100 via the network 300, when the user specifies the Web site address (such as URL) provided from the hepatic disease-evaluating apparatus 100, via the input device 250 on the screen displaying Web browser 211. Specifically, when the user instructs update of the browser 211 screen on the client apparatus 200, the Web browser 211 sends the Web site's URL using a particular protocol via the communication IF 280, transmits an instruction demanding transmission of the Web page corresponding to the amino acid concentration data transmission screen to the hepatic disease-evaluating apparatus 100 based on the routing of the URL.

Then upon receipt of the instruction from the client apparatus 200, the instruction-analyzing part 102*a* in hepatic disease-evaluating apparatus 100 analyzes the transmitted instruction and sends the instruction to other parts in the controlling device 102 according to the analytical result. When the transmitted instruction is an instruction to send the Web page corresponding to the amino acid concentration data transmission screen, the browsing processing part 102*b* mainly obtains the Web data for display of the Web page stored in a particular region of the memory device 106 and sends the Web data to the client apparatus 200 via the communication interface 104. Specifically, upon receiving the Web page transmission instruction by the user, the controlling device 102 in the hepatic disease-evaluating apparatus 100 demands input of user ID and user password from the user. If the user ID and password are input, the authentication-processing part 102*c* examines the input user ID and password by comparing them with the user ID and user password stored in the user information file 106*a* for authentication, and the browsing processing part 102*b* sends the Web data to the client apparatus 200, only when the user is authenticated. The client apparatus 200 is identified with the IP (Internet Protocol) address transmitted from the client apparatus 200 together with the transmission instruction.

Then, the client apparatus 200 receives in the receiving part 213 the Web data transmitted from the hepatic disease-evaluating apparatus 100 via the communication IF 280, examines the Web data with the Web browser 211, and displays the amino acid concentration data transmission screen on the monitor 261. The instruction demanding transmission of screen from the client apparatus 200 to the hepatic disease-evaluating apparatus 100, the transmission of the Web data from the hepatic disease-evaluating apparatus 100 to the client apparatus 200 and the display of the Web page in the client apparatus 200 are performed almost similarly, and thus, detailed description will be omitted below.

When the user inputs and selects the amino acid concentration data of the subject to be evaluated via the input device 250 of client apparatus 200, the sending part 214 of the client apparatus 200 sends an identifier for identifying input information and selected items to the hepatic disease-evaluating apparatus 100 (step SA-1). Thus, the user can send the amino acid concentration data of the subject to be evaluated to the hepatic disease-evaluating apparatus 100. In step SA-1, transmission of the amino acid concentration data to the hepatic disease-evaluating apparatus 100 may be performed, for example, by using an existing file transfer technology such as FTP (File Transfer Protocol).

After the processing in step SA-1, the hepatic disease-evaluating apparatus 100 may analyze the identifier transmitted from the client apparatus 200 and the instruction from the client apparatus 200 in the instruction-analyzing part 102*a* and send an instruction demanding transmission of the index formula used in calculation of the index to the database apparatus 400; and the database apparatus 400 may analyze the instruction sent form the hepatic disease-evaluating apparatus 100 in the instruction-analyzing part 402*a* and send the index formula (specifically updated newest index) stored in a particular region of the memory device 406 to the hepatic disease-evaluating apparatus 100 via the communication interface 404.

The hepatic disease-evaluating apparatus 100 then receives the amino acid concentration data transmitted from the client apparatuses 200 via the communication interface 104 in the receiving part 102*f*, stores the received amino acid concentration data in a particular region of the amino acid concentration data file 106*b*, and executes [3-2. hepatic disease evaluation processing] described below (step SA-3).

The sending-part 102*f* of the hepatic disease-evaluating apparatus 100 then sends the evaluation results (evaluation results concerning the disease state of the hepatic disease of the subject to be evaluated) obtained in step SA-3 to the client apparatus 200 that has sent the amino acid concentration data of the subject to be evaluated and the database apparatus 400 (step SA-4). Specifically, the hepatic disease-evaluating apparatus 100 first generates a Web page for display of evaluation results in the Web page-generating part 102 and stores it in a particular memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing instruction to the hepatic disease-evaluating apparatus 100. The hepatic disease-evaluating apparatus 100 then examines the browsing instruction transmitted from the client apparatus 200 in the browsing processing part 102*a* and reads the Web page out of the memory device 106. The hepatic disease-evaluating apparatus 100 then sends Web data corresponding to the read-out Web page to the client apparatus 200 from the sending part 102*f*. The hepatic disease-evaluating apparatus 100 may send only the evaluation results or the data same as the Web data sent to the client apparatus 200 to the database apparatus 400.

In step SA-4, the hepatic disease-evaluating apparatus 100 may notify the evaluation results to the user client apparatus 200 by electronic mail. Specifically, the hepatic disease-evaluating apparatus 100 first acquires the user electronic mail address in the electronic mail-generating part 102*d* at the transmission timing for example based on the user ID, with reference to the user information stored in the user information file 106*a*. The hepatic disease-evaluating apparatus 100 then generates electronic mail data including user name and evaluation result, with the electronic mail address obtained as its mail address in the electronic mail-generating part 102*d*. The hepatic disease-evaluating apparatus 100 then sends the generated data from the sending part 102*j*. Also in step SA-4, the hepatic disease-evaluating apparatus 100 may send the evaluation results to the user client apparatus 200 by using an existing file transfer technology such as FTP.

Then, the controlling device 402 in the database apparatus 400 receives the evaluation results or the Web data transmitted from the hepatic disease-evaluating apparatus 100 via the communication interface 404 and stores (accumulates) the evaluation results or the Web data in a particular memory region of the memory device 406 (step SA-5).

The receiving part 213 of the client apparatus 200 receives the Web data transmitted from the hepatic disease-evaluating apparatus 100 via the communication IF 280, analyzes the received Web data with the Web browser 211, and outputs the Web page screen displaying the evaluation result on the monitor 261 (step SA-6).

In this way, the user knows the evaluation results concerning the disease state of the hepatic disease of the subject to be evaluated by browsing the Web page displayed on the monitor 261 of client apparatus 200. The user can print out the content of the Web page displayed on the monitor 261 in a printer 262. When the evaluation results are sent from the hepatic disease-evaluating apparatus 100 by electronic mail, the user can receive the transmitted electronic mail at any timing in the electronic mailer 212 of the client apparatus 200, and display the received electronic mail on the monitor 261 with the known function of the electronic mailer 212. The user may print out the content of the electronic mail displayed on the monitor 261 in the printer 262.

These are description of the hepatic disease evaluation service processing.

[3-2. Hepatic Disease Evaluation Processing]

Hereinafter, an example of the hepatic disease evaluation processing performed in the hepatic disease-evaluating apparatus 100 will be described in detail with reference to FIG. 13. FIG. 13 is a flowchart showing an example of the hepatic disease evaluation processing performed in the hepatic disease-evaluating apparatus 100.

First, data unpreferred in calculating the index (data including defective values or many outliers) are removed from the amino acid concentration data received in the controlling device 102 in step SA-2 (step SB-1: data editing).

Then in the index-calculating part 102*g*, the index indicating the degree of hepatic fibrosis is calculated from the amino acid concentration data edited in step SB-1, based on one or more indices previously stored in a particular memory region of the index database 106*c* (an index or a combination of plurality of indices), and the index is stored in a particular memory region of the index file 106*d* (step SB-2).

The index used in step SB-2 has a numerator of its fractional expressions including at least one of Phe and Tyr and at least one of Thr, Met and Orn and a denominator of the fractional expressions including at least one of Val, Leu and Ile and at least one of Pro and Gly, or the numerator of the fractional expressions including at least one of Val, Leu and Ile and at least one of Pro and Gly and the denominator of the fractional expressions including at least one of Phe and Tyr and at least one of Thr, Met and Orn.

Alternatively, the index used in step SB-2 may be specifically the sum of two fractional expressions; the numerator in one fractional expression is any one of Phe and Tyr and the denominator in the one fractional expression is any one of Val, Leu, and Ile; and the numerator in the other fractional expression is the sum of at least one of Thr, Met and Orn, and the denominator of the other fractional expression is the sum of at least one of Pro and Gly. Alternatively, the index used in step SB-2 may be, in particular, the sum of the two fractional expressions, and the numerator in one fractional expression is Phe and the denominator in the one fractional expression, Val; and the numerator in the other fractional expression is the sum of Thr, Met and Orn and the denominator of the other fractional expression, the sum of Pro and Gly.

Then, the disease state of the hepatic disease of the subject to be evaluated is evaluated in the disease state-evaluating part 102*h*, based on the index calculated in step SB-2, and the evaluation results are stored in a particular memory region of the evaluation result file 106*e* (step SB-3). Here in step SB-3, it may be determined whether the progressive stage of hepatic fibrosis of the subject to be evaluated is in the stage of F0, F1, or F2, or in the stage of F3 or F4, by comparing the index calculated in step SB-2 with a previously set particular threshold value (cutoff value). Alternatively, it may be determined whether the progressive stage of hepatic fibrosis of the subject to be evaluated is in the stage of F0, F1, F2, or F3 or in the stage of F4 by comparing the index calculated in step SB-2 with the previously set particular threshold value (cutoff value).

These are description of the hepatic disease evaluation processing.

As described above, in the hepatic disease-evaluating apparatus 100, the index indicating the degree of hepatic fibrosis is calculated from the amino acid concentration data of the subject to be evaluated including the amino acid concentration values based on the one or more indices of the fractional expressions having the amino acid concentrations as the variables, and the disease state of the hepatic disease of the subject to be evaluated is evaluated, based on the index value. The index used in the calculation of the index has the numerator of the fractional expressions including at least one of Phe and Tyr and at least one of Thr, Met and Orn and the denominator of the fractional expressions including at least one of Val, Leu and Ile and at least one of Pro and Gly, or the numerator of the fractional expressions including at least one of Val, Leu and Ile and at least one of Pro and Gly and the denominator of the fractional expressions including at least one of Phe and Tyr and at least one of Thr, Met and Orn. Thus, it is possible to evaluate progress of the disease state of hepatic disease accurately and to determine, for example, whether treatment with interferon/ribavirin combination is needed to patients with a hepatic disease accurately. Specifically, it is possible to determine whether the hepatic fibrosis of a patient is in the stage of F0, F1, or F2, or in the stage of F3 or F4 accurately. It is also possible specifically to determine whether the hepatic fibrosis of a patient is in the stage of F0, F1, F2, or F3, or in the stage of F4 accurately.

The gold standard method for diagnosis of stepwise progress of hepatic fibrosis or liver cirrhosis has been performed with the use of hepatic biopsy or laparoscopy, and the indicator consisting of stages of F0, F1, F2, F3, and F4 by the METAVIR scoring method has been used as the fibrosis stage indicator. The stage F0 is a state without fibrosis; fibrosis starts at the stages F1, and progresses to the stages F2 and F3; and the stage F4 is the final disease stage of liver cirrhosis. Such an invasive diagnosis exerts a burden such as pain on the patient and also may cause risks such as bleeding by the test. Accordingly, there exists a need for a non-invasive diagnostic method. Proposed as the non-invasive diagnostic methods are methods using blood platelet, globulin, AST, ALT, albumin, hyaluronic acid, and the like alone or in combination as an index (e.g., "Luo J. C., Hwang S. J., Chang F. Y., Chu C. W., Lai C. R., Wang Y. J., Lee P. C., Tsay S. H., and Lee S. D., Simple blood tests can predict compensated liver cirrhosis in patients with chronic hepatitis C. Hepatogastroenterology 49, 478 (2002)", "Pohl A., Behling C., Oliver D., Kilani M., Monson P., and Hassanein T., Serum aminotransferase levels and platelet counts as predictors of degree of fibrosis in chronic hepatitis C virus infection. Am. J. Gastroenterol, 96, 3142 (2001)", "Wai C. T., Greenson J. K, Fontana R. J., Kalbfleisch J. D., Marrero J. A., Conjeevaram H. S., and Lok A. S., A simple noninvasive index can predict both significant fibrosis and cirrhosis in patients with chronic hepatitis C. Hepatology, 38, 518 (2003)", and others). There are still some indices lower in diagnostic performance and demanding further improvement among these indices. In addition, some of them is accompanied by analytical complexity demanding plurality of proteins in quantitative determination (e.g., "Fibrotest; Biopredictive, Houilles, France, U.S. patent application Ser. No. 09/687,459").

Although the Fischer ratio "(Leu+Val+Ile)/(Phe+Tyr)" proposed by Fischer is known as an index using blood amino acid concentration in diagnosis of hepatic disease (BTR ratio "(Leu+Val+Ile)/Tyr", which is a simplified Fischer ratio, is also used in clinical diagnosis for the same purpose with the Fischer ratio), it is only used in diagnosis of hepatic encephalopathy in the patients with liver cirrhosis ("J. E. Fischer, J. M. Funovics, A. Aguirre, J. H. James, J. M. Keane, R. I. Wesdorp, N. Yoshimura, and T. Westman, The role of plasma amino acids in hepatic encephalopathy, Surgery 78 (1975) 276-290"). The index described in International Publication WO2004/052,191 filed by the present applicant is also known as a method of diagnosing hepatitis using blood amino acid, but it is an index aimed at differentiating the stage F0 from the stages other than F0.

For clinical purpose, there exists a need for a method of discriminating the progressive stage of fibrosis and determining whether the treatment with interferon/ribavirin combination is needed. In particular, there is a need for discriminating two groups: stage F0, F1, or F2 and stage F3 or F4, or stage F0, F1, F2, or F3 and stage F4.

After intensive studies to meet the clinical need, the inventors have found that there is significant correlation between an index using blood amino acid concentration and the progress of hepatic disease, especially hepatic fibrosis, and completed the present invention. Accordingly, the present invention provides a novel index satisfying the clinical need as a useful index, and it is possible to evaluate progress of the disease state of hepatic disease accurately and determine, for example, whether treatment with interferon/ribavirin combination is needed to patients with a hepatic disease accurately, by using the hepatic disease-evaluating apparatus 100. Specifically, it is possible to determine whether the hepatic fibrosis of a patient is in the stage of F0, F1, or F2 or in the stage of F3 or F4 accurately. Specifically, it is also possible to determine whether the hepatic fibrosis of a patient is in the stage of F0, F1, F2 or F3 or in the stage of F4 accurately. The hepatic disease-evaluating apparatus 100 allows diagnosis of hepatic diseases, in particular disease state of hepatitis, chronic hepatitis, hepatic fibrosis, and liver cirrhosis, more easily and accurately than traditional methods.

The index formula used in calculation of the index according to the present invention may be the sum of two fractional expressions; the numerator in one fractional expression is any one of Phe and Tyr and the denominator in the one fractional expression is any one of Val, Leu, and Ile; and the numerator in, the other fractional expression is the sum of at least one of Thr, Met and Orn and the denominator of the other fractional expression is the sum of at least one of Pro and Gly. The index formula used in calculation of the index may be, in particular, the sum of the two fractional expressions; the numerator in the one fractional expression is Phe and the denominator in the one fractional expression is Val; and the numerator in the other fractional expression is the sum of Thr, Met and Orn and the denominator of the other fractional expression is the sum of Pro and Gly. It is thus possible to evaluate progress of the disease state of hepatic disease more accurately and determine, for example, whether treatment with interferon/ribavirin combination is needed to patients with a hepatic disease more accurately. Specifically, it is possible to determine whether the hepatic fibrosis of a patient is in the stage of F0, F1, or F2 or in the stage of F3 or F4 more accurately. Specifically, it is also possible to determine whether the hepatic fibrosis of a patient is in the stage of F0, F1, F2, or F3 or in the stage of F4 more accurately.

According to the present invention, the hepatic disease includes at least one of hepatitis, chronic hepatitis, hepatic fibrosis and liver cirrhosis, and thus, it is possible to apply the present invention suitably to clinically, frequently required evaluation of the disease state of at least one of diseases such as hepatitis, chronic hepatitis, hepatic fibrosis and liver cirrhosis.

In addition to the embodiments above, various different embodiments of the present invention are possible within the technological scope of the Claims. For example, among the processings described in the embodiments above, all or part of the processings described above as performed automatically may be performed manually, and all or part of the manually-conducted processings may be performed automatically by known methods. In addition, the processing procedure, control procedure, typical name, various registered data, information including parameters such as retrieval condition, screen, and database configuration shown in the description above or drawings may be modified arbitrarily, unless specified otherwise. For example, the components of the hepatic disease-evaluating apparatus 100 shown in the figures are conceptual functionally and may not be the same physically as those shown in the figure. In addition, all or part of the operational function of each component and each device in the hepatic disease-evaluating apparatus 100 (in particular, processings in controlling device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may not be an independent program, and may be operated together with plurality of modules and libraries or with a different program such as OS (Operating System). The program is stored on a recording medium and read mechanically as needed by the hepatic disease-evaluating apparatus 100. Any well-known configuration or procedure may be used for reading the programs recorded on the recording medium in each apparatus and for reading procedure and installation of the procedure after reading.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk); and the like. Examples of the "fixed physical media" include various media installed in a computer system such as ROM, RAM, and HD. The "communication media" are, for example, media storing the program for a short period of time such as communication line and carrier wave when the program is transmitted via a network such as LAN (Local Area Network), WAN (Wide Area Network), or the Internet.

EXAMPLE 1

Figure 14:
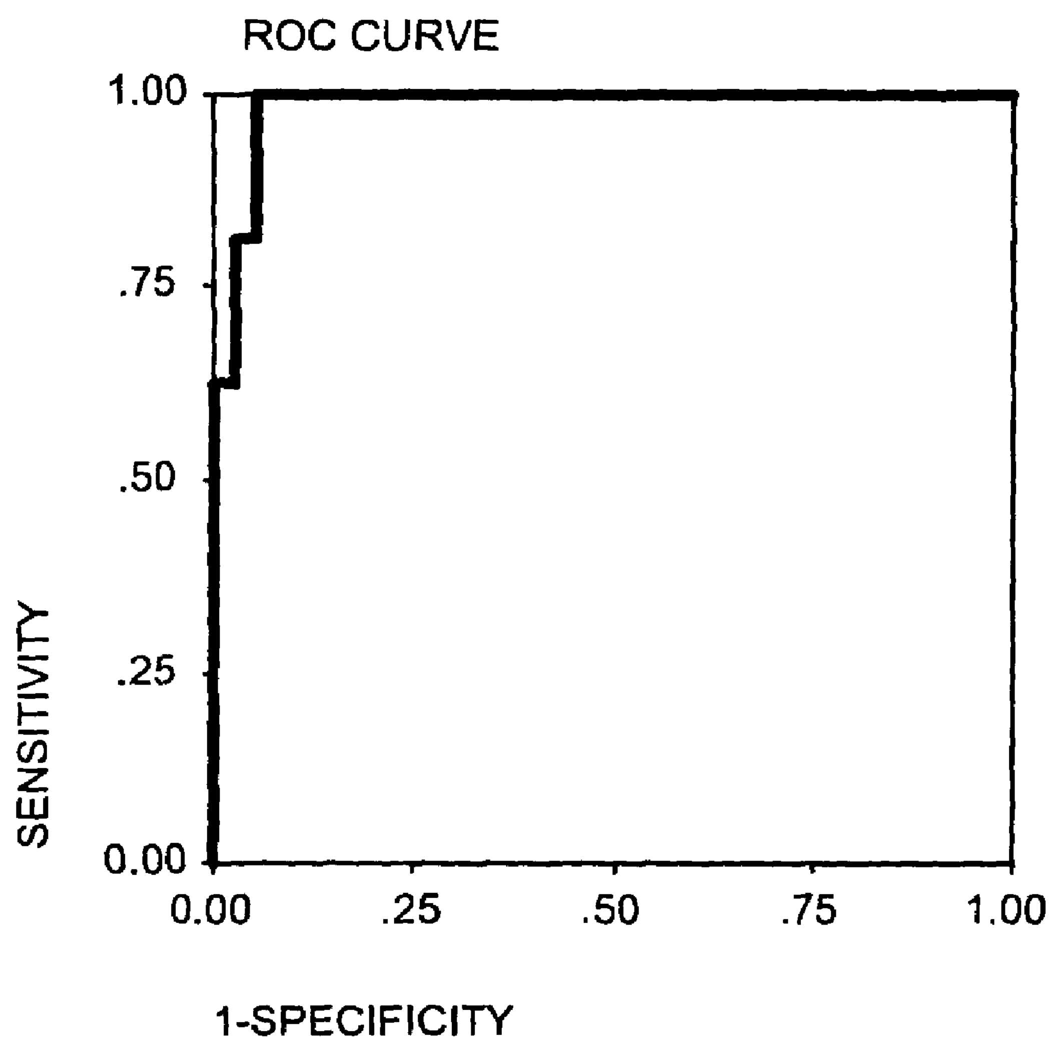
FIG. 14 is a graph showing the ROC (Receiver Operating Characteristic) curve for evaluation of the diagnostic performance of index 1 in discrimination of two groups "F0, F1, F2, or F3" and "F4"

In Example 1, diagnosis results obtained by hepatic biopsy and those obtained according to the index concerning whether the progressive stage of hepatic fibrosis of a patient with hepatitis C is in the stage of F0, F1, F2, or F3 or in the stage of F4 were compared. After intensive studies to maximize the efficiency of discriminating the two groups: "F0, F1, F2, or F3" and "F4" concerning the progressive stage of hepatic fibrosis, an index 1: "(Phe)/(Val)+(Thr+Met+Orn)/(Pro+Gly)" was obtained as such an index. The diagnostic performance of the index 1 for discrimination of the two groups: "F0, F1, F2, or F3" and "F4" was evaluated by using the AUC (Area Under Curve) of the ROC curve (Receiver Operating Characteristic Curve) shown in FIG. 14. In diagnosis according to the index 1, the blood amino acid concentration, as determined from the blood samples of hepatitis C patients diagnosed by hepatic biopsy by using the amino acid analysis method described in the embodiment above was used.

As a result, the AUC of index 1 was 099±001 (95% confidence interval: 0.96 to 1.00). On the other hand, discrimination of two groups "F0, F1, F2, or F3" and "F4" according to the Fischer ratio "(Leu+Val+Ile)/(Phe+Tyr)" was performed, and the diagnostic performance was evaluated with the AUC of ROC curve, similarly to the index 1, giving an AUC of 0.91±0.04 (95% confidence interval: 0.83 to 0.99). As shown in FIG. 16, the sensitivity was 81%; the specificity, 96%; the positive predictive value, 87%; and the negative predictive value, 92%, in discrimination of two groups "F0, F1, F2, or F3" and "F4" by using the index 1, when the cutoff value was 1.10.

As apparent, the index 1 was found to be a useful index higher in diagnostic performance (typically, superior in diagnostic performance to the Fischer ratio) in discrimination of two groups "F0, F1, F2, or F3" and "F4".

EXAMPLE 2

Figure 15:
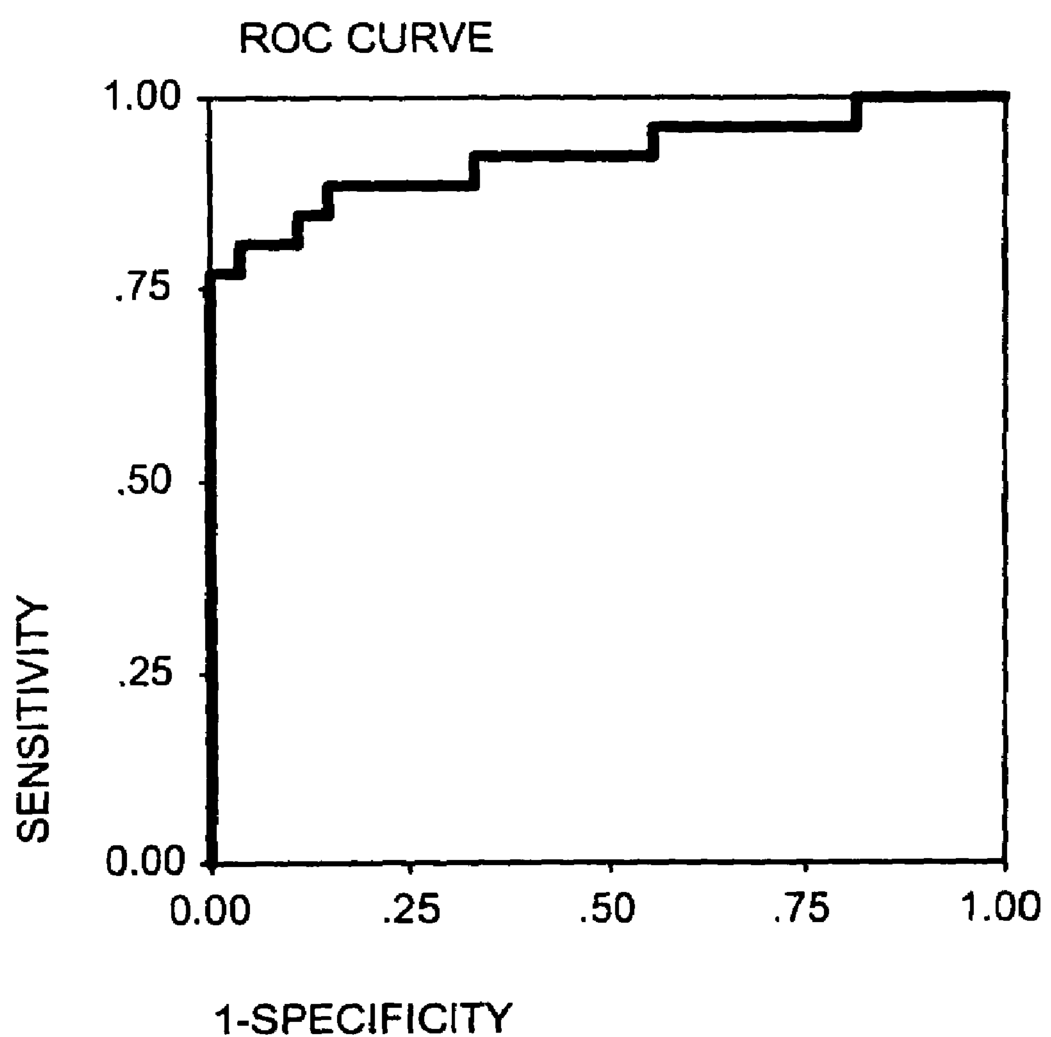
FIG. 15 is a graph showing the ROC curve for evaluation of the diagnostic performance of index 1 in discrimination of two groups "F0, F1, or F2" and "F3 or F4"

In Example 2, the diagnosis results obtained by hepatic biopsy and those obtained according to the index concerning whether the progressive stage of hepatic fibrosis of a patient with hepatitis C is in the stage of F0, F1, or F2 or in the stage of F3 or F4 were compared. After intensive studies to maximize the efficiency of discriminating the two groups: "F0, F1, or F2" and "F3 or F4" concerning the progressive stage of hepatic fibrosis, an index 1 "(Phe)/(Val)+(Thr+Met+Orn)/(Pro+Gly)" was obtained as such an index, similarly to Example 1. The diagnostic performance of the index 1 for discrimination of the two groups "F0, F1, or F2" and "F3 or F4" was evaluated by using the AUC (Area Under Curve) of the ROC curve (Receiver Operating Characteristic Curve) shown in FIG. 15. In the diagnosis according to the index 1, the blood amino acid concentration used in Example 1 was used.

As a result, the AUC of index 1 was 0.92±0.04 (95% confidence interval: 0.84 to 1.00). On the other hand, discrimination of two groups "F0, F1, or F2" and "F3 or F4" according to the Fischer ratio "(Leu+Val+Ile)/(Phe+Tyr)" was performed and the diagnostic performance was evaluated with the AUC of ROC curve similarly to the index 1, giving an AUC of 0.87±0.05 (95% confidence interval: 0.77 to 0.96). As shown in FIG. 16, the sensitivity was 89%; the specificity, 88%; the positive predictive value, 79%; and the negative predictive value, 88%, in discrimination of two groups "F0, F1, or F2" and "F3 or F4" by using the index 1, when the cutoff value was 0.95.

As apparent, the index 1 was found to be a useful index higher in diagnostic performance in discrimination of two groups "F0, F1, or F2" and "F3 or F4" (especially, superior in diagnostic performance to the Fischer ratio).

EXAMPLE 3

In Example 3, the diagnosis results obtained by hepatic biopsy and those obtained according to the index concerning whether the progressive stage of hepatic fibrosis of a patient with hepatitis C is in the stage of F0, F1, F2, or F3 or in the stage of F4 were compared. After intensive studies to maximize the efficiency of discriminating the two groups: "F0, F1, F2, or F3" and "F4" concerning the progressive stage of hepatic fibrosis, the indices shown in FIGS. 17 to 20 were obtained as indices having a diagnostic performance (discrimination efficiency) similar to the index 1 in Example 1 or 2. The diagnostic performance of the indices shown in FIGS. 17 to 20 in discrimination of two groups "F0, F1, F2, or F3" and "F4" were evaluated by using the AUC of ROC curve. The blood amino acid concentration used in Example 1 or 2 was used in diagnosis according to the index.

As a result, in discrimination of two groups "F0, F1, F2, or F3" and "F4" by using the indices shown in FIGS. 17 to 20, it is possible to obtain a sensitivity and a specificity for each index shown in FIGS. 17 to 20, by selecting a cutoff value optimizing the diagnostic performance.

As apparent, the indices shown in FIGS. 17 to 20 were found to be useful indices higher in diagnostic performance in discrimination of two groups "F0, F1, F2, or F3" and "F4". The fact that the diagnostic performance of each index shown in FIGS. 17 to 20 is equivalent to the diagnostic performance of index 1 in discrimination of two groups "F0, F1, F2, or F3" and "F4" seemingly indicates that the correlation coefficient between Phe and Tyr is high, the correlation coefficient among Val, Leu, and Ile is high, or the correlation coefficient among the indices obtained by replacing (Thr+Met+Orn) with one or two of Thr, Met, and Orn and (Pro+Gly) with one of Pro and Gly or the indices in combination of any substitution above is high.

EXAMPLE 4

In Example 4, the diagnosis results obtained by hepatic biopsy and those obtained according to the index concerning whether the progressive stage of hepatic fibrosis of a patient with hepatitis C is in the stage of F0, F1, or F2 or in the stage of F3 or F4 were compared. After intensive studies to maximize the efficiency of discriminating the two groups: "F0, F1, or F2" and "F3 or F4" concerning the progressive stage of hepatic fibrosis, indices shown in FIGS. 17 to 20 were obtained as the indices having a diagnostic performance (discrimination efficiency) similar to the index 1 in Examples 1 or 2. The diagnostic performance of the indices shown in FIGS. 17 to 20 in discrimination of the two groups "F0, F1, or F2" and "F3 or F4" was evaluated by using the AUC (Area Under Curve) of the ROC curve. In the diagnosis according to the index, the blood amino acid concentration used in Examples 1, 2 or 3 was used.

As a result, the sensitivity and the specificity shown in FIGS. 17 to 20 were obtained for each index, by selecting a cut off value optimal for diagnostic performance, in discrimination of two groups "F0, F1, or F2" and "F3 or F4" by using the indices shown in FIGS. 17 to 20.

As apparent, the indices shown in FIGS. 17 to 20 were found to be useful indices higher in diagnostic performance in discrimination of two groups "F0, F1, or F2" and "F3 or F4". The fact that the diagnostic performance of each index shown in FIGS. 17 to 20 is equivalent to the diagnostic performance of index 1 in discrimination of two groups "F0, F1, or F2" and "F3 or F4" seemingly indicates that the correlation coefficient between Phe and Tyr is high, the correlation coefficient among Val, Leu, and Ile is high, or the correlation coefficient among the indices obtained by replacing (Thr+Met+Orn) with one or two of Thr, Met, and Orn and (Pro+Gly) with one of Pro and Gly or the indices in combination of any substitution above is high.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A hepatic disease-evaluating apparatus, comprising:

an index calculating unit that calculates an index indicating a degree of hepatic fibrosis from amino acid concentration data obtained from a patient with hepatitis, wherein the data includes amino acid concentration values, based on one or more indices having amino acid concentration as a variable; and a disease state evaluating unit that evaluates a disease state of the patient with hepatitis, based on the index calculated by the index calculating unit, wherein the index has amino acid concentration variables for at least two amino acids selected from the group consisting of Phe, Tyr, Val, Leu, Ile, Thr, Met, Orn, Pro, and Gly.

2. The hepatic disease-evaluating apparatus according to claim 1, wherein the index has amino acid concentration variables for at least one of Phe, Tyr, Val, Leu and Ile, and at least one of Thr, Met, Orn, Pro, and Gly.

3. The hepatic disease-evaluating apparatus according to claim 1, wherein the index has amino acid concentration variables for at least one of Phe and Tyr, at least one of Val, Leu, and Ile, and at least one of Thr, Met, Orn, Pro, and Gly.

4. The hepatic disease-evaluating apparatus according to claim 1, wherein the index has amino acid concentration variables for at least one of Phe, Tyr, Val, Leu, and Ile, at least one of Thr, Met and Orn, and at least one of Pro and Gly.

5. The hepatic disease-evaluating apparatus according to claim 1, wherein the index has amino acid concentration variables for at least one of Phe and Tyr, at least one of Val, Leu, and Ile, at least one of Thr, Met, and Orn, and at least one of Pro and Gly.

6. The hepatic disease-evaluating apparatus according to claim 1, wherein the index includes a fractional expression, which has (i) a numerator including an amino acid concentration variable for at least one of Phe and Tyr and at least one of Thr, Met, and Orn and a denominator including an amino acid concentration variable for at least one of Val, Leu, and Ile and at least one of Pro and Gly, or (ii) a numerator including an amino acid concentration variable for at least one of Val, Leu, and Ile and at least one of Pro and Gly and a denominator including an amino acid concentration variable for at least one of Phe and Tyr and at least one of Thr, Met, and Orn.

7. The hepatic disease-evaluating apparatus according to claim 6, wherein the index is a sum of two fractional expressions;

the numerator in one fractional expression is an amino acid concentration variable for any one of Phe and Tyr and the denominator in one fractional expression is an amino acid concentration variable for any one of Val, Leu, and Ile; and the numerator in the other fractional expression is a sum of amino acid concentration variables for at least one of Thr, Met, and Orn and the denominator of the other fractional expression is a sum of amino acid concentration variables for at least one of Pro and Gly.

8. The hepatic disease-evaluating apparatus according to claim 7, wherein the index is the sum of the two fractional expressions; the numerator in the one fractional expression is an amino acid concentration variable for Phe and the denominator in the one fractional expression is an amino acid concentration variable for Val; and the numerator in the other fractional expression is the sum of amino acid concentration variables for Thr, Met, and Orn and the denominator of the other fractional expression is the sum of amino acid concentration variables for Pro and Gly.

9. The hepatic disease-evaluating apparatus according to claim 1, wherein the hepatic disease includes at least one of chronic hepatitis and liver cirrhosis.

10. The hepatic disease-evaluating apparatus according to claim 1, wherein the disease state evaluating unit evaluates the disease state of the patient with hepatitis by (i) determining whether the progressive stage of hepatic fibrosis to be evaluated is in the stage of F0, F1, or F2, or in the stage of F3 or F4; or (ii) determining whether the progressive stage of hepatic fibrosis to be evaluated is in the stage of F0, Fl, F2, or F3 or in the stage of F4, based on the index calculated by the index calculating unit.

11. A hepatic disease-evaluating method, comprising:

an index calculating step of calculating an index indicating a degree of hepatic fibrosis from amino acid concentration data obtained from a patient with hepatitis, wherein the data includes amino acid concentration values, based on one or more indices having amino acid concentration as a variable; and a disease state evaluating step of evaluating a disease state of the patient with hepatitis, based on the index calculated at the index calculating step, wherein the index has amino acid concentration variables for at least two of Phe, Tyr, Val, Leu, Ile, Thr, Met, Orn, Pro, and Gly, and wherein the disease state evaluating step is carried out with a computer.

12. The hepatic disease-evaluating method according to claim 11, wherein the index has amino acid concentration variables for at least one of Phe, Tyr, Val, Leu and Ile, and at least one of Thr, Met, Orn, Pro, and Gly.

13. The hepatic disease-evaluating method according to claim 11, wherein the index has amino acid concentration variables for at least one of Phe and Tyr, at least one of Val, Leu, and Ile, and at least one of Thr, Met, Orn, Pro, and Gly.

14. The hepatic disease-evaluating method according to claim 11, wherein the index has amino acid concentration variables for at least one of Phe, Tyr, Val, Leu, and Ile, at least one of Thr, Met and Orn, and at least one of Pro and Gly.

15. The hepatic disease-evaluating method according to claim 11, wherein the index has amino acid concentration variables for at least one of Phe and Tyr, at least one of Val, Leu, and Ile, at least one of Thr, Met, and Orn, and at least one of Pro and Gly.

16. The hepatic disease evaluating method according to claim 11, wherein the index includes a fractional expression, which has (i) a numerator including an amino acid concentration variable for at least one of Phe and Tyr and at least one of Thr, Met, and Orn and a denominator including an amino acid concentration variable for at least one of Val, Leu, and Ile and at least one of Pro and Gly, or (ii) a numerator including an amino acid concentration variable for at least one of Val, Leu, and Ile and at least one of Pro and Gly and a denominator including an amino acid concentration variable for at least one of Phe and Tyr and at least one of Thr, Met, and Orn.

17. The hepatic disease-evaluating method according to claim 16, wherein the index is a sum of two fractional expressions;

the numerator in one fractional expression is an amino acid concentration variable for any one of Phe and Tyr and the denominator in one fractional expression is an amino acid concentration variable for any one of Val, Leu, and Ile; and the numerator in the other fractional expression is a sum of amino acid concentration variables for at least one of Thr, Met, and Orn and the denominator of the other fractional expression is a sum of amino acid concentration variables for at least one of Pro and Gly.

18. The hepatic disease evaluating method according to claim 17, wherein the index is the sum of the two fractional expressions; the numerator in the one fractional expression is an amino acid concentration variable for Phe and the denominator in the one fractional expression is an amino acid concentration variable for Val; and the numerator in the other fractional expression is the sum of amino acid concentration variables for Thr, Met, and Orn and the denominator of the other fractional expression is the sum of amino acid concentration variables for Pro and Gly.

19. The hepatic disease-evaluating apparatus according to claim 1, wherein the hepatic disease includes at least one of chronic hepatitis and liver cirrhosis.

20. The hepatic disease evaluating method according to claim 11, wherein the disease state evaluating unit evaluates the disease state of the patient with hepatitis by (i) determining whether the progressive stage of hepatic fibrosis to be evaluated is in the stage of F0, Fl, or F2, or in the stage of F3 or F4; or (ii) determining whether the progressive stage of hepatic fibrosis to be evaluated is in the stage of F0, Fl, F2, or F3 or in the stage of F4, based on the index calculated by the index calculating unit.

21. A hepatic disease-evaluating system, comprising a hepatic disease-evaluating apparatus that evaluates a hepatic disease and an information communication terminal apparatus that provides amino acid concentration data obtained from a patient with hepatitis, wherein the data includes amino acid concentration values, which hepatic disease-evaluating apparatus and the information communication terminal apparatus that are connected to each other communicatively via a network, wherein the information communication terminal apparatus comprises:

a sending unit that sends the amino acid concentration data to be evaluated to the hepatic disease-evaluating apparatus; and a receiving unit that receives evaluation results of a disease state of the hepatic disease to be evaluated sent from the hepatic disease-evaluating apparatus, the hepatic disease-evaluating apparatus comprises:

a receiving unit that receives the amino acid concentration data to be evaluated sent from the information communication terminal apparatus;

an index calculating unit that calculates an index indicating the degree of hepatic fibrosis from the amino acid concentration data to be evaluated received by the receiving unit, based on one or more indices having amino acid concentration as a variable;

a disease state evaluating unit that evaluates the disease state of the patient with hepatitis, based on the index calculated by the index calculating unit; and a sending unit that sends the evaluation results obtained by the disease state evaluating unit to the information communication terminal apparatus, wherein the index has amino acid concentration variables for at least two of Phe, Tyr, Val, Leu, Ile, Thr, Met, Orn, Pro and Gly.

22. The hepatic disease-evaluating system according to claim 21, wherein the index has amino acid concentration variables for at least one of Phe, Tyr, Val, Leu and Ile, and at least one of Thr, Met, Orn, Pro, and Gly.

23. The hepatic disease-evaluating system according to claim 21, wherein the index has amino acid concentration variables for at least one of Phe and Tyr, at least one of Val, Leu, and Ile, and at least one of Thr, Met, Orn, Pro, and Gly.

24. The hepatic disease-evaluating system according to claim 21, wherein the index has amino acid concentration variables for at least one of Phe, Tyr, Val, Leu, and Ile, at least one of Thr, Met and Orn, and at least one of Pro and Gly.

25. The hepatic disease-evaluating system according to claim 21, wherein the index has amino acid concentration variables for at least one of Phe and Tyr, at least one of Val, Leu, and Ile, at least one of Thr, Met, and Orn, and at least one of Pro and Gly.

26. The hepatic disease evaluating system according to claim 21, wherein the index includes a fractional expression, which has (i) a numerator including an amino acid concentration variable for at least one of Phe and Tyr and at least one of Thr, Met, and Orn and a denominator including an amino acid concentration variable for at least one of Val, Leu, and Ile and at least one of Pro and Gly, or (ii) a numerator including an amino acid concentration variable for at least one of Val, Leu, and Ile and at least one of Pro and Gly and a denominator including an amino acid concentration variable for at least one of Phe and Tyr and at least one of Thr, Met, and Orn.

27. The hepatic disease-evaluating system according to claim 26, wherein the index is a sum of two fractional expressions;

the numerator in one fractional expression is an amino acid concentration variable for any one of Phe and Tyr and the denominator in one fractional expression is an amino acid concentration variable for any one of Val, Leu, and Ile; and the numerator in the other fractional expression is a sum of amino acid concentration variables for at least one of Thr, Met, and Orn and the denominator of the other fractional expression is a sum of amino acid concentration variables for at least one of Pro and Gly.

28. The hepatic disease evaluating system according to claim 27, wherein the index is the sum of the two fractional expressions; the numerator in the one fractional expression is an amino acid concentration variable for Phe and the denominator in the one fractional expression is an amino acid concentration variable for Val; and the numerator in the other fractional expression is the sum of amino acid concentration variables for Thr, Met, and Orn and the denominator of the other fractional expression is the sum of amino acid concentration variables for Pro and Gly.

29. The hepatic disease-evaluating apparatus according to claim 21, wherein the hepatic disease includes at least one of chronic hepatitis and liver cirrhosis.

30. The hepatic disease evaluating system according to claim 21, wherein the disease state evaluating unit evaluates the disease state of the patient with hepatitis by (i) determining whether the progressive stage of hepatic fibrosis to be evaluated is in the stage of F0, F1, or F2, or in the stage of F3 or F4; or (ii) determining whether the progressive stage of hepatic fibrosis to be evaluated is in the stage of F0, F1, F2, or F3 or in the stage of F4, based on the index calculated by the index calculating unit.

31. A tangible computer-readable medium having a hepatic disease-evaluating program for executing on a computer a hepatic disease-evaluating method, comprising:

an index calculating step of calculating an index indicating a degree of hepatic fibrosis from amino acid concentration data obtained from a patient with hepatitis, wherein the data includes amino acid concentration values, based on one or more indices having amino acid concentration as a variable; and a disease state-evaluating step of evaluating a disease state of the patient with hepatitis, based on the index calculated at the index calculating step, wherein the index has at least two amino acid concentration variables for amino acids selected from the group consisting of Phe, Tyr, Val, Leu, Ile, Thr, Met, Orn, Pro and Gly.

32. The tangible computer-readable medium according to claim 31, wherein the index has amino acid concentration variables for at least one of Phe, Tyr, Val, Leu and Ile, and at least one of Thr, Met, Orn, Pro, and Gly.

33. The tangible computer-readable medium according to claim 31, wherein the index has amino acid concentration variables for at least one of Phe and Tyr, at least one of Val, Leu, and Ile, and at least one of Thr, Met, Orn, Pro, and Gly.

34. The tangible computer-readable medium according to claim 31, wherein the index has amino acid concentration variables for at least one of Phe, Tyr, Val, Leu, and Ile, at least one of Thr, Met and Orn, and at least one of Pro and Gly.

35. The tangible computer-readable medium according to claim 31, wherein the index has amino acid concentration variables for at least one of Phe and Tyr, at least one of Val, Leu, and Ile, at least one of Thr, Met, and Orn, and at least one of Pro and Gly.

36. The tangible computer-readable medium according to claim 31, wherein the index includes a fractional expression, which has (i) a numerator including an amino acid concentration variable for at least one of Phe and Tyr and at least one of Thr, Met, and Orn and a denominator including an amino acid concentration variable for at least one of Val, Leu, and Ile and at least one of Pro and Gly, or (ii) a numerator including an amino acid concentration variable for at least one of Val, Leu, and Ile and at least one of Pro and Gly and a denominator including an amino acid concentration variable for at least one of Phe and Tyr and at least one of Thr, Met, and Orn.

37. The tangible computer-readable medium according to claim 36, wherein the index is a sum of two fractional expressions;

the numerator in one fractional expression is an amino acid concentration variable for any one of Phe and Tyr and the denominator in one fractional expression is an amino acid concentration variable for any one of Val, Leu, and Ile; and the numerator in the other fractional expression is a sum of amino acid concentration variables for at least one of Thr, Met, and Orn and the denominator of the other fractional expression is a sum of amino acid concentration variables for at least one of Pro and Gly.

38. The tangible computer-readable medium according to claim 37, wherein the index is the sum of the two fractional expressions; the numerator in the one fractional expression is an amino acid concentration variable for Phe and the denominator in the one fractional expression is an amino acid concentration variable for Val; and the numerator in the other fractional expression is the sum of amino acid concentration variables for Thr, Met, and Orn and the denominator of the other fractional expression is the sum of amino acid concentration variables for Pro and Gly.

39. The hepatic disease-evaluating apparatus according to claim 31, wherein the hepatic disease includes at least one of chronic hepatitis and liver cirrhosis.

40. The tangible computer-readable medium according to claim 31, wherein the disease state evaluating unit evaluates the disease state of the patient with hepatitis by (i) determining whether the progressive stage of hepatic fibrosis to be evaluated is in the stage of F0, F1, or F2, or in the stage of F3 or F4; or (ii) determining whether the progressive stage of hepatic fibrosis to be evaluated is in the stage of F0, Fl, F2, or F3 or in the stage of F4, based on the index calculated by the index calculating unit.

41. An information communication terminal apparatus communicably connected via a network to a hepatic disease-evaluating apparatus that evaluates hepatic disease, comprising:

a sending unit that sends amino acid concentration data to be evaluated to the hepatic disease evaluating apparatus, wherein the data are obtained from a patient with hepatitis; and a receiving unit that receives evaluation results of a disease state of the patient with hepatitis sent from the hepatic disease evaluating apparatus, wherein the evaluation results are the results of calculating an index indicating the degree of hepatic fibrosis from the amino acid concentration data to be evaluated, based on one or more indices having amino acid concentration as a variable, and evaluating the disease state of patient with hepatitis, based on the calculated index, wherein the index has at least two amino acid concentration variables for amino acids selected from the group consisting of Phe, Tyr, Val, Leu, Ile, Thr, Met, Orn, Pro, and Gly.

42. A hepatic disease evaluating apparatus communicably connected via a network to a information communication terminal apparatus that provides amino acid concentration data obtained from a patient with hepatitis, wherein the data include amino acid concentration values, comprising:

a receiving unit that receives the amino acid concentration data to be evaluated sent from the information communication terminal apparatus;

an index calculating unit that calculates an index indicating a degree of hepatic fibrosis from the amino acid concentration data to be evaluated received by the receiving unit, based on one or more indices having amino acid concentration as a variable;

a disease state evaluating unit that evaluates a disease state of the patient with hepatitis, based on the index calculated by the index calculating unit; and a sending unit that sends evaluation results obtained by the disease state evaluating unit to the information communication terminal, apparatus, wherein the index has at least two amino acid concentration variables for amino acids selected from the group consisting of Phe, Tyr, Val, Leu, Ile, Thr, Met, Orn, Pro, and Gly.

* * * * *